United States Patent [19]

Hirai et al.

[11] Patent Number: 4,705,737

[45] Date of Patent: Nov. 10, 1987

[54] HEAT DEVELOPABLE PHOTOGRAPHIC MATERIALS

[75] Inventors: Hiroyuki Hirai; Kozo Sato; Yoshiharu Yabuki; Ken Kawata, all of Kanagawa, Japan

[73] Assignee: Fuji Photo Film Co., Ltd., Kanagawa, Japan

[21] Appl. No.: 767,405

[22] Filed: Aug. 20, 1985

Related U.S. Application Data

[63] Continuation-in-part of Ser. No. 688,651, Jan. 3, 1985, abandoned, which is a continuation-in-part of Ser. No. 590,388, Mar. 16, 1984, abandoned, and a continuation-in-part of Ser. No. 732,323, May 9, 1985, abandoned.

[30] Foreign Application Priority Data

Mar. 16, 1983 [JP] Japan .................................. 58-43861
May 9, 1984 [JP] Japan .................................. 59-92558
Aug. 20, 1984 [JP] Japan .................................. 59-172956

[51] Int. Cl.$^4$ .......................... G03C 5/54; G03C 1/40
[52] U.S. Cl. .................................... 430/203; 430/351; 430/617; 430/619; 430/559; 430/955
[58] Field of Search ............... 430/203, 351, 353, 617, 430/619, 955, 559

[56] References Cited

U.S. PATENT DOCUMENTS

| | | | |
|---|---|---|---|
| 3,220,846 | 11/1965 | Tinker et al. | 430/617 |
| 4,060,420 | 11/1977 | Merkel et al. | 430/955 |
| 4,088,496 | 5/1978 | Merkel | 430/955 |
| 4,500,626 | 2/1985 | Naito et al. | 430/203 |
| 4,514,493 | 4/1985 | Hirai et al. | 430/617 |

FOREIGN PATENT DOCUMENTS 16844159 9/1984 Japan .
17483059 10/1984 Japan .

OTHER PUBLICATIONS

Research Disclosure, No. 151, Nov. 1976, Altland et al., pp. 9-11, Disclosure No. 15109.

*Primary Examiner*—Richard L. Schilling
*Attorney, Agent, or Firm*—Sughrue, Mion, Zinn, Macpeak, and Seas

[57] ABSTRACT

A heat developable photographic material comprising a support having thereon at least a photosensitive silver halide, a binder, and at least on of base precursors represented by following formula (I) or (II):

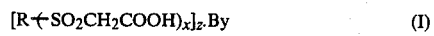

$$[R(SO_2CH_2COOH)_x]_z \cdot B_y \quad (I)$$

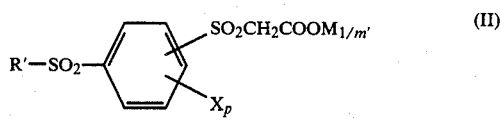

(II)

wherein R represents an alkyl group, an alkylene group, an aryl group, an arylene group, a monovalent or divalent heterocyclic group, each of which may be unsubstituted or substituted; B represents a mono- or di-acidic, nitrogen-containing, sulfur-free base having a pKa of not lower than about 7 and containing 12 carbon atoms or less; x is an integer of 1 when R represents a monovalent group or an integer of 2 when R represents a divalent group, y is the same as x when B represents the mono-acidic base or an integer of 1 when B represents the di-acidic base; and z is an integer of 2 when R represents a monovalent group and B represents the di-acidic base or otherwise an integer of 1; R' represents an alkyl group, a cycloalkyl group, an alkenyl group, an alkynyl group, an aralkyl group, an aryl group or a heterocyclic group, each of which may be substituted or unsubstituted; X represents a substituent; p represents an integer of 0 to 4; and m' represents the valence number of M whereby stability with the passge of time prior to heat development is improved.

20 Claims, No Drawings

HEAT DEVELOPABLE PHOTOGRAPHIC MATERIALS

CROSS REFERENCE TO RELATED APPLICATIONS

This is continuation-in-part application of Ser. No. 688,651 filed Jan. 3, 1985, now abandoned, which is a continuation-in-part application Ser. No. 590,388 filed Mar. 16, 1984, now abandoned, and Ser. No. 732,323 filed May 9, 1985 now abandoned.

FIELD OF THE INVENTION

The present invention relates to a heat developable photographic material, and more particularly to a novel photographic material containing a novel base precursor. The "base precursor" in the present invention is a material releasing a basic component by thermal decomposition.

The present invention also relates to a novel heat developable process using such a heat developable photographic material.

DEVELOPMENT OF THE INVENTION

Since the photographic process using silver halide has excellent photographic properties such as sensitivity and gradation control as compared with other photographic processes, such as, for example, an electrophotographic process and a diazo photographic process, the silver halide photographic process has been most widely used. Recently, however, a technique of easily and rapidly obtaining images by employing a dry process such as heating, etc., as the image-forming process of a photographic material using silver halide in place of a conventional wet processing using developing solution, etc., has been developed.

Heat developable photographic materials are known in the art and heat developable color photographic materials and processes for processing these photographic materials are described in, for example, *Shashin Kogaku no Kiso* (Basis for Photographic Engineering), pages 553-555, published by Corona K.K., 1979; *Eizo Joho* (Image Formation), page 40, published April, 1978; *Nebletts Handbook of Photography and Reprography*, 7th Ed., pages 32-33, published by Van Nostrand Reinhold Company; U.S. Pat. Nos. 3,152,904, 3,301,678, 3,392,020 and 3,457,075; U.K. Pat. Nos. 1,131,108 and 1,167,777; and *Research Disclosure*, June 1978, pages 9-15 (RD-17029).

Various processes of obtaining color images using a heat developable system have been proposed. For example, a process for forming color images by the combination of the oxidation product of a developing agent and couplers involving p-phenylenediamine reducing agent and phenolic or active methylene couplers are described in U.S. Pat. No. 3,531,286; p-aminophenol reducing agents are described in U.S. Pat. No. 3,761,270; sulfonamidophenol reducing agents are described in Belgian Pat. No. 802,519 and *Research Disclosure*, September 1975, pages 31 and 32; and the combination of sulfonamidophenol reducing agents and 4-equivalent couplers are described in U.S. Pat. No. 4,021,240.

However, these processes have the disadvantage that turbid color images are formed since reduced silver images and the color images are simultaneously formed at the unexposed and undeveloped areas after heat development. To overcome this disadvantage, a process of removing the silver images by liquid treatment and a process of transferring the dye only onto another layer, for example, a sheet having an image-receiving layer have been proposed, however, it is not easy to discriminate the dye from unreacted materials and transfer only the dye.

Also, a process of introducing a nitrogen-containing heterocyclic group into a dye, forming a silver salt, and liberating the dye by heat development in the presence of the silver salt is described in *Research Disclosure*, May 1978, pages 54-58 (RD-16966). However, in this process, clear images cannot be obtained since it is difficult to control the liberation of dye at the unexposed areas and hence the process is unsuitable for general use.

Furthermore, a process of forming positive color images using heat-sensitive silver dye bleaching process is known with useful dyes and bleaching processes being described in, for example, *Research Disclosure*, April 1976, pages 30-32 (RD-14433); ibid., December 1976, pages 14-15 (RD-15227); U.S. Pat. No. 4,235,957, etc.

However, the foregoing processes have the disadvantages that an additional step of superposing an activating agent sheet followed by heating is required for accelerating the bleaching of the dye and also the color image formed is gradually bleached by reduction due to free silver which is present during storage of the color image mateial for a long period of time.

Also, a process of producing color images utilizing leuco dyes is described in, for example, U.S. Pat. Nos. 3,985,565 and 4,022,617. However, the process has the disadvantage that it is difficult to retain leuco dyes in photographic materials in a stable manner and hence the photographic material gradually becomes colored during storage.

Most of these heat developable processes in the prior art are common in that final images are produced in the same area as that of other photographic components including the unexposed silver halide are present. For example, silver halide which still remains unexposed and undeveloped in the final image area is gradually exposed even after the image formation concludes and, changes to a dark color to cause stain or turbidity in color as mentioned above. This exposure and change is unwanted because such damages faithful color reproduction of images. Such a phenomenon is well known in the art and, various attempts have been made to overcome such a disadvantage caused by the co-presence of photographic components with the final images. In U.S. Pat. No. 3,301,678, certain sulfur-containing compounds are used as stabilizer precursors to stabilize the final images. The sulfur-containing compound breaks down or cleaves at elevated temperatures to form a compound that combines with the silver halide in the unexposed and undeveloped areas. Further in U.S. Pat. No. 4,060,420, α-sulfonylacetates that release, upon heating, sulfur- and nitrogen-containing activator-stabilizers are used to stabilize silver images.

Heat developable photographic materials usually contain a base or base precursor in the photographic materials for accelerating the development by heating. Also, in this case, it is preferred to use a base precursor capable of releasing a basic material by heat decomposition from the viewpoint of the shelf life of the photographic materials.

Typical examples of the base precursor are described in U.K. Pat. No. 998,949. Preferred base precursors are salts of carboxylic acids and organic bases. Useful carboxylic acid includes trichloroacetic acid, trifluoroacetic acid, etc., and useful organic base includes guanidine, piperidine, morpholine, p-toluidine, 2-picoline, etc. Guanidine trichloroacetate described in U.S. Pat. No. 3,220,846 is particularly useful for such a purpose. Also, the aldonic amides described in Japanese Patent Application (OPI) No. 22,625/75 (the term "OPI" indicates an unexamined published patent application laid open to public inspection) and U.S. Pat. No. 4,463,079 are decomposed at high temperature to form a base and are preferably used.

However, many of these base precursors require a relatively long period of time for obtaining images and cause severe fog. Also, these base precursors have the disadvantages that they are easily influenced by air and humidity, to decompose and change photographic characteristics of the photographic material, or greatly reduce the shelf life of the photographic materials containing them.

For overcoming such a disadvantage, α-sulfonylacetates are proposed in Japanese Patent Application (OPI) No. 168441/84, U.S. Pat. No. 4,060,420, etc. These materials are excellent from the viewpoint of providing images in a short period of time, but are still not totally sufficient in providing high density, or cause a side action of forming severe fog, as shown by a comparative data hereinafter. The α-sulfonylacetates, typically 2-amino-2-thiazolium phenylsulfonylacetates, disclosed as activator-stabilizer precursors in U.S. Pat. No. 4,060,420 should release, upon heating, sulfur- and nitrogen-containing activator-stabilizers. In this prior art system, it is very important to release the compound containing both sulfur and nitrogen in the molecule thereof. Particularly the presence of sulfur in the molecule is indispensable for stabilizing the silver image since the finally viewed silver image is co-present with the unexposed and undeveloped silver halide, as mentioned above, in a white-and-black or monocolor photographic system. Further, some of the above-described base precursors are insufficient with respect to the shelf life of the light-sensitive material before heat development.

The present inventors have discovered a novel heat developable process which final color images are optically or physically or by any other means separated from the silver images and from other photographic components including the unexposed and undeveloped silver halide which do not take part in forming the final color images. A series of applications based on this novel process have been filed by a group of the present inventors, now matured into U.S. Pat. Nos. 4,463,079, 4,500,626, etc. These processes are novel and advantageous in that no consideration is given either on the silver image or on the unexposed and undevloped silver halide usually viewed together with the final silver images in the prior art and thus adversely affecting image reproduction.

SUMMARY OF THE INVENTION

An object of the present invention is to overcome the disadvantages of conventional materials as described above and to provide a heat developable photographic material capable of giving images of high density in a short period of time in a substantially water free state.

Another object of the present invention is to provide a heat developable photographic material containing a novel base precursor capable of providing images having high density and minimized fog.

A further object of the present invention is to provide a heat developable photographic material excellent in stability with the passage of time. The term "stability with the passage of time" refers to the time during storage of a heat developable photographic material before heat development, the heat developable photographic material shows less change of photographic performance such as the maximum density, the minimum density, the sensitivity, etc.

A still further object of the present invention is to provide a heat developable color photographic material containing a base precursor which is suited for applying to a heat developing process capable of releasing a mobile, hydrophilic dye thereby to view dye images separated from silver images or other photographic components unnecessary for completing the dye images.

Yet another object of the present invention is to provide a simple heat developing process for forming color images, using such a heat developable color photographic material, which are optically or physically separated from silver images or other photographic components unnecessary for forming the color images.

It has now been discovered that the above-described objects of the present invention can be attained by the heat developable photographic material containing at least one of compounds represented by formula (I) or (II):

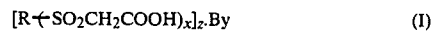

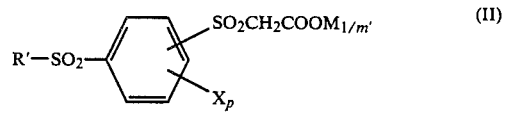

wherein R represents an alkyl group, an alkylene group, an aryl group, an arylene group, a monovalent or divalent heterocyclic group, each of which may be unsubstituted or substituted; B represents a mono- or di-acidic, nitrogen-containing, sulfur-free base having a pKa of not lower than about 7 and containing 12 carbon atoms or less; x is an integer of 1 when R represents a monovalent group or an integer of 2 when R represents a divalent group, y is the same as x when B represents the mono-acidic base or an integer of 1 when B represents the di-acidic base; and z is an integer of 2 when R represents a monovalent group and B represents the di-acidic base or otherwise an integer of 1; R' represents an alkyl group, a cycloalkyl group, an alkenyl group, an alkynyl group, an aralkyl group, an aryl group or a heterocyclic group, each of which may be substituted or unsubstituted; X represents a substituent; p represents an integer of 0 to 4; M represents an alkali metal or an alkaline earth metal and m' represents the valence number of M.

DESCRIPTION OF PREFERRED EMBODIMENTS

The present invention provides a heat developable photographic material comprising a support having thereon at least a light-sensitive silver halide, a binder, and at least one of base precursors represented by formula (I) or (II) described above.

In the present invention, it is important that the base precursor can release the N-containing, heterocyclic S-free base. If the base contains sulfur in the molecule thereof, it would be extremely difficult to obtain images of high maximum density by this heat developable process. This finding is quite contrary to the teaching of the prior art in which heterocyclic S-containing base precursors such as 2-amino-2-thiazolium phenylsulfonylacetates are effective. The effect brought by the heterocyclic S-containing base precursor is believed to be because images are viewed as silver images (white-and-black or monocolor images) in the same layer where the unexposed and undeveloped silver halide is present and the unexposed and undeveloped silver halide is stabilized by forming silver mercaptide through some interaction between the silver halide and the sulfur from the thiazolium base precursor.

On the other hand, in the present invention a base is released, and the base accelerates heat-development of the photographic material. Therefore, mechanism and effects of the action of the base are completely different from those of prior arts.

In formula (I), the alkyl group preferably has 1 to 22 carbon atoms, the alkylene group preferably has 1 to 22 carbon atoms, the aryl group preferably has 6 to 22 carbon atoms, the arylene group preferably has 6 to 22 carbon atoms and the monovalent or divalent heterocyclic group is preferably a 5- or 6-membered heterocyclic group containing N, S and/or O as hetero atom(s) or its condensed ring group, each of which may be unsubstituted or substituted.

Preferred condensed heterocyclic group for R includes the above-mentioned heterocyclic groups condensed with a benzene ring.

Preferred examples of R include an aryl group, an arylene group, a monovalent or divalent heterocyclic group and substituted counterparts of these groups. Particularly preferred examples of R include aryl groups or heterocyclic groups (including condensed heterocyclic groups) substituted with an electron attracting group having a Hammet sigma value of above 0 (for example, a halogen atom, a cyano group, a nitro group, a substituted or unsubstituted carbamoyl group, a substituted or unsubstituted sulfamoyl group, an alkoxycarbonyl group, a sulfonyl group, e.g., a substituted or unsubstituted alkyl sulfonyl group, etc.).

Specific examples of R include a methylene group, an ethylene group, a phenyl group, a p-chlorophenyl group, a p-bromophenyl group, a p-iodophenyl group, a 3,4-dichlorophenyl group, a 2,5-dichlorophenyl group, a 2,4-dichlorophenyl group, a 3-nitrophenyl group, a 4-nitrophenyl group, a 4-cyanophenyl group, a 3-carbamoylphenyl group, a 3-sulfamoylphenyl group, a 2-methoxycarbonylphenyl group, a 3-methoxycarbonylphenyl group, a 1-naphthyl group, a 2-naphthyl group, a 2-pyridyl group, a 4-pyridyl group, a 2-thienyl group, a 5-chloro-2-thienyl group, a 2-benzimidazolyl group, a 1,3-phenylene group, a 1,5-naphthylene group, a 2,6-naphthylene group, a 2,7-naphthylene group, etc.

In addition to the preferred examples of R described above, most preferred R is represented by formula:

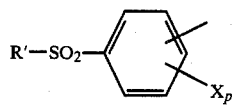

and thus, when the base portion is shown by $B_{1/m}$, represented by formula (I'):

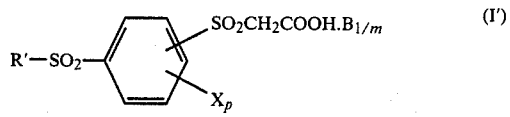

(I')

wherein R', X, p and B are as defined above and; m represents 1 when B represents mono-acidic base and represents 2 when B represents di-acidic base.

In formulae (I') and (II), the alkyl group, cycloalkyl group, alkenyl group and alkynyl group represented by R' preferably have from 1 to 8 carbon atoms, and the aralkyl group and aryl group represented by R' preferably have at most 8 carbon atoms. It is preferred that the heterocyclic ring shown by R' has at least one of nitrogen atom, an oxygen atom and a sulfur atom as a hetero atom of a 5- or 6-membered heterocyclic ring. Each group represented by R' may by substituted and preferred examples of the substituent are an alkyl group, an alkyl or aryl sulfonyl group, a sulfamoyl group, an N-alkyl or N-arylsulfamoyl group, a carbamoyl group, an N-alkyl or N-arylcarbamoyl group, an alkyl or arylsulfonamido group, an alkyl or arylcarbonylamino group, a halogen atom, and $-OM_{1/m'}$, $-COOM_{1/m'}$, $-OH.B_{1/m}$, (wherein $-OH$ is phenolic), and $-COOH.B_{1/m}$, (wherein M, B, m and m' have same definitions as shown hereinabove) etc. These substituents may further have a substituent selected from groups disclosed hereinafter as preferred examples of X.

Specific examples of the groups shown by R' are a methyl group, an ethyl group, a butyl group, an octyl group, a 2-ethylhexyl group, a phenyl group, a p-chlorophenyl group, a p-bromophenyl group, a p-methylphenyl group, a m-(diethylsulfamoyl)phenyl group, a 1-naphthyl group, a 2-naphthyl group, a benzyl group, a pyridyl group, a pyrazolyl group, an imidazolyl group, etc.

Of the base portion represented by B, it is desirable that B is a base which is conventionally used in a heat developable light-sensitive material, that is, a mono- or di-acidic base having a pKa value of 7 or higher and having not more than 12 carbon atoms, and B is preferably a low volatile base having pKa value of 10 or higher and a boiling point of not lower than 150° C. More preferably, B represents organic bases, especially, a mono- or di-acidic nitrogen-containing, sulfur-free base, for example, aromatic or aliphatic amines or diamines, piperidines, piperadines, guanidines, cyclic guanidines, amidines, cyclic amidines, tetraalkylammonium hydroxides, etc. Preferred examples of B are dimethylamine, diethylamine, piperidine, piperadine, ethylenediamine, N,N'-dimethylethylenediamine, acetamidine, diazabicyclononene, diazabicycloundecene, tetramethylammonium hydroxide, tetraethylammonium hydroxide,

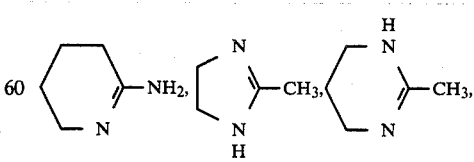

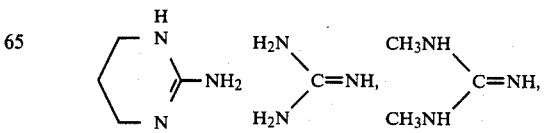

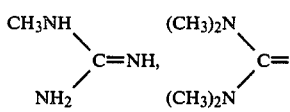

tetramethylethylenediamine, N,N,N'N'-tetramethyltetramethylenediamine, etc.

Preferred examples of X are a hydrogen atom, a halogen atom, an alkyl group, a cycloalkyl group, an aralkyl group, an alkoxy group, an aryloxy group, an aryl group, an alkyl or aryl-carbonylamino group, an alkyl- or arylcarbonyl group, a cyano group, an alkylsulfonylamino group, a nitro group, an arylsulfonylamino group, an alkylsulfonyl group, an arylsulfonyl group, a sulfamoyl group, a substituted sulfamoyl group, a carbamoyl group, a substituted carbamoyl group, an alkylthio group, an arylthio group, an alkoxycarbonyl group, an aryloxycarbonyl group, an alkyl or aryl acyloxy group, $-OM_{1/m}$, $-COOM_{1/m'}$, $-OH.B_{1/m}$ (wherein —OH is a phenolic), $-COOH.B_{1/m}$, wherein M, B, m and m' have same definitions as defined hereinabove. In these groups, an alkyl group and an aryl group may be further substituted.

Preferred examples of M are Na+, K+, Cs+, Ba++, etc.

It is preferred that the carboxymethylsulfonyl group be at a para-position to the position of the sulfonyl group ($RSO_2-$).

Specific examples of the base precursors shown by formula (I) are illustrated below together with preparation of representative compounds; preferred base precursors shown by formula (I') will be separately exemplified hereinafter also together with preparation of representative compounds.

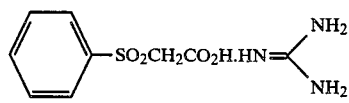 (1)

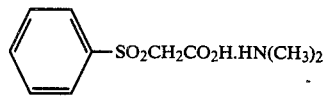 (2)

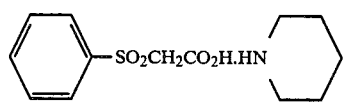 (3)

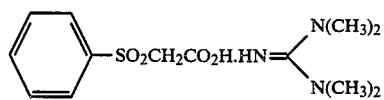 (4)

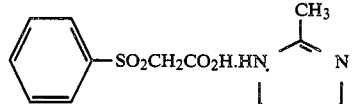 (5)

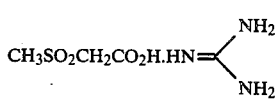 (6)

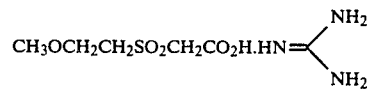 (7)

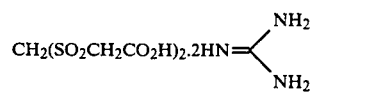 (8)

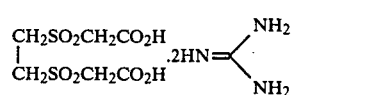 (9)

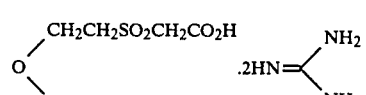 (10)

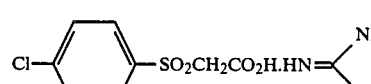 (11)

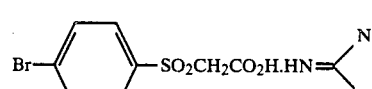 (12)

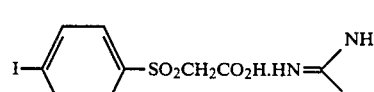 (13)

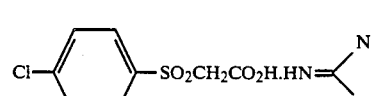 (14)

 (15)

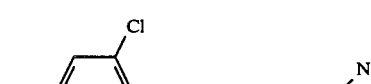 (16)

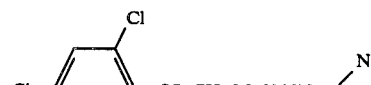 (17)

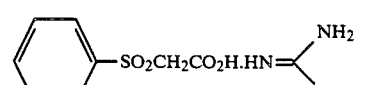 (18)

-continued
(19) 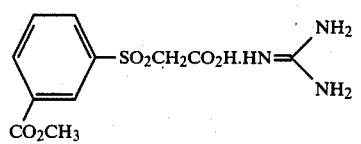
(20) 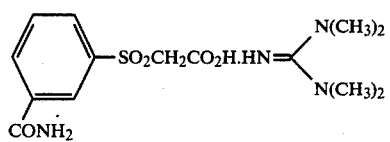
(21) 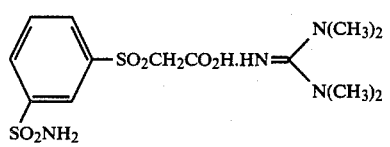
(22) 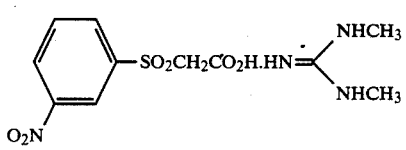
(23) 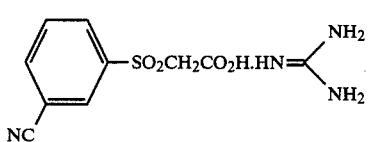
(24) 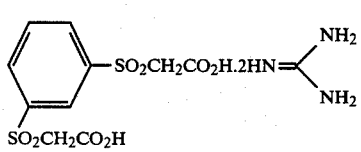
(25) 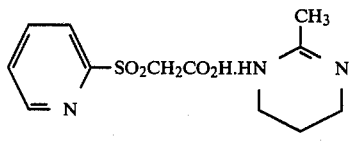
(26) 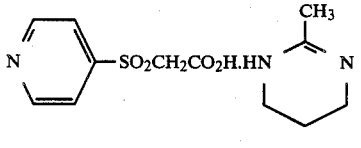
(27) 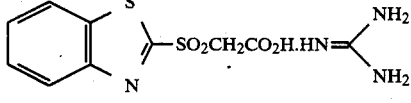
(28) 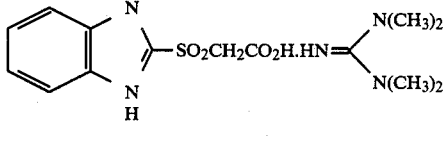
(29) 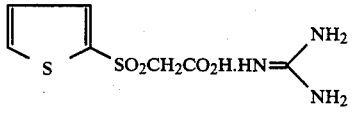
-continued
(30) 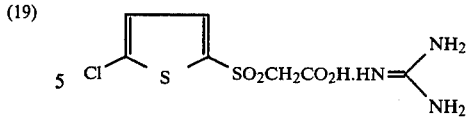
(31) 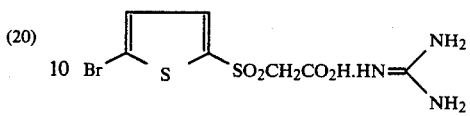
(32) 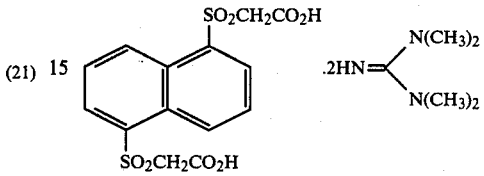
(33) 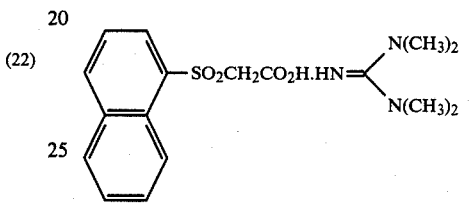
(34) 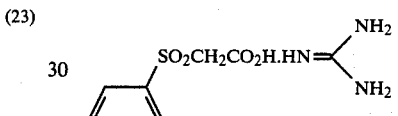
(35) 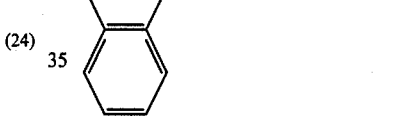
(36) 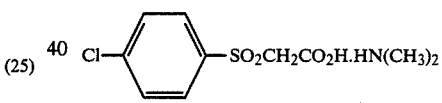
(37) 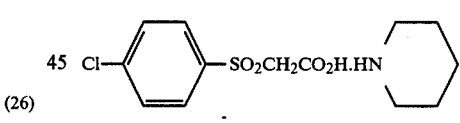
(38) 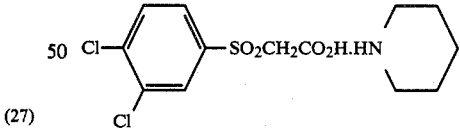
(39) 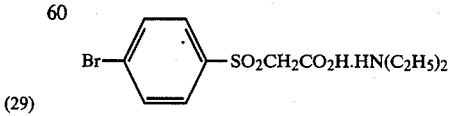
(40) 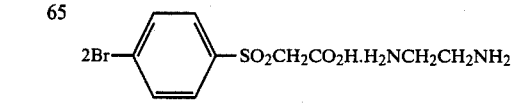

-continued

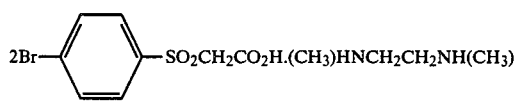
(41)

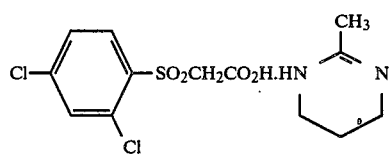
(42)

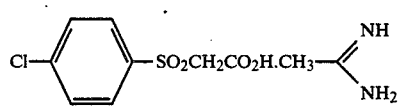
(43)

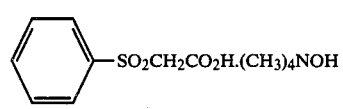
(44)

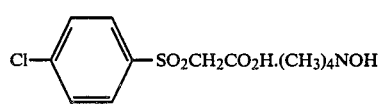
(45)

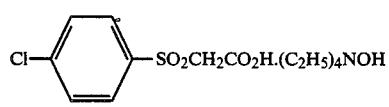
(46)

(A) The α-sulfonylacetate represented by the general formula (I) can generally be prepared by condensing a sulfinic acid with an α-haloacetic acid ester to form an α-sulfonylacetic acid ester, subjecting this ester to hydrolysis with an alkali at room temperature to obtain an α-sulfonylacetic acid and converting the acid to its salt in a conventional method.

The synthesis of examples of the base precursors of the present invention are shown below. Unless otherwise indicated, all parts percents, ratios and the like are by weight.

SYNTHESIS EXAMPLE 1

Synthesis of Base Precursor (1)

A mixture of 60 g of sodium benzenesulfinate dihydrate, 33.4 g of ethyl bromoacetate and 300 ml of methanol was heated under reflux for 2 hours. After the methanol was distilled off under reduced pressure, water and ethyl acetate were added and the organic layer formed was separated. The organic layer was washed with water and dried followed by distilling off the ethyl acetate under reduced pressure to obtain 43.3 g of ethyl phenylsulfonyl acetate as a pale yellow liquid.

The ester thus obtained was added to a 15% potassium hydroxide aqueous solution and the mixture was stirred at room temperature for 1 hour. While cooling with ice, the mixture was neutralized with diluted hydrochloric acid and extracted with ethyl acetate. The organic layer was separated, washed with water and dried. Distilling off the ethyl acetate under reduced pressure gave rise to 28 g of phenylsulfonylacetic acid as colorless crystals.

A mixture of 20 g of phenylsulfonylacetic acid, 9 g of guanidine carbonate and 100 ml of methanol was stirred at room temperature for 1 hour. Distilling off methanol (at a temperature of 50° C. or less) afforded 25.5 g of Base Precursor (1). Melting point (decomp): 137°–138° C.

SYNTHESIS EXAMPLE 2

Synthesis of Base Precursor (11)

To a mixture of 504 g of sodium sulfite and 1.8 l of water was added portionwise 16 g of p-chlorobenzenesulfonyl chloride at 50° C. After being stirred at 55°–60° C. for 3 hours, the mixture was cooled with ice and white crystals which separated out were collected and washed with cold water to obtain 152 g of sodium p-chlorobenzenesulfinate. In a manner similar to Synthesis Example 1, sodium p-chlorobenzenesulfinate and ethyl chloroacetate were reacted to obtain ethyl p-chlorophenylsulfonyl acetate. The ester thus obtained (110 g) was added portionwise to a 20% sodium hydroxide aqueous solution while cooling with ice. During this procedure, white crystals separated out quickly. After stirring at room temperature for 1 hour, the mixture was cooled with ice and white crystals were collected by filtration and washed with isopropanol. The crystals thus obtained were dissolved in 300 ml of water and the solution was neutralized with diluted hydrochloric acid. The white crystals which separated out were collected by filtration, washed with water to obtain 90 g of p-chlorophenylsulfonylacetic acid.

A mixture of 82 g of p-chlorophenylsulfonylacetic acid, 31.5 g of guanidine carbonate, 200 ml of methanol and 100 ml of water was stirred at room temperature for 3 hours. The white crystals which separated out were collected by filtration and washed with methanol to obtain 88 g of Base Precursor (11). Melting point (decomp.): 147°–148° C.

The following are preferred examples of the base precursors shown by formula (I') and (II) which can be used in the present invention.

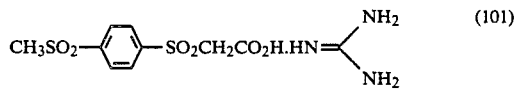
(101)

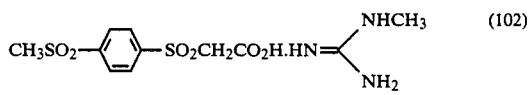
(102)

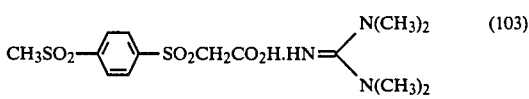
(103)

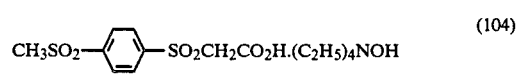
(104)

(105)

(106)

(107)

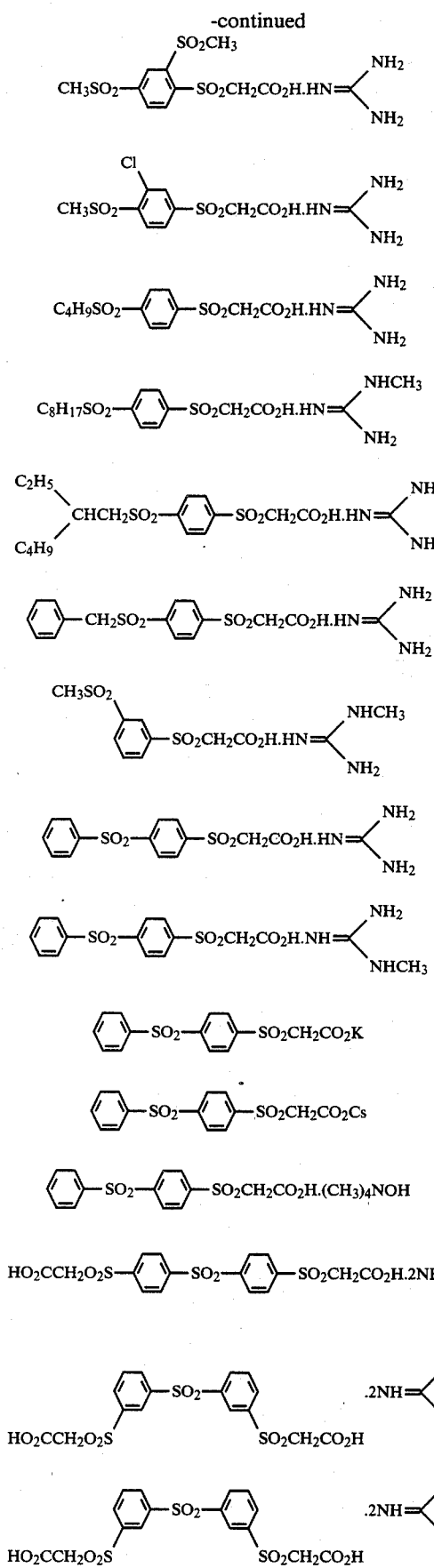
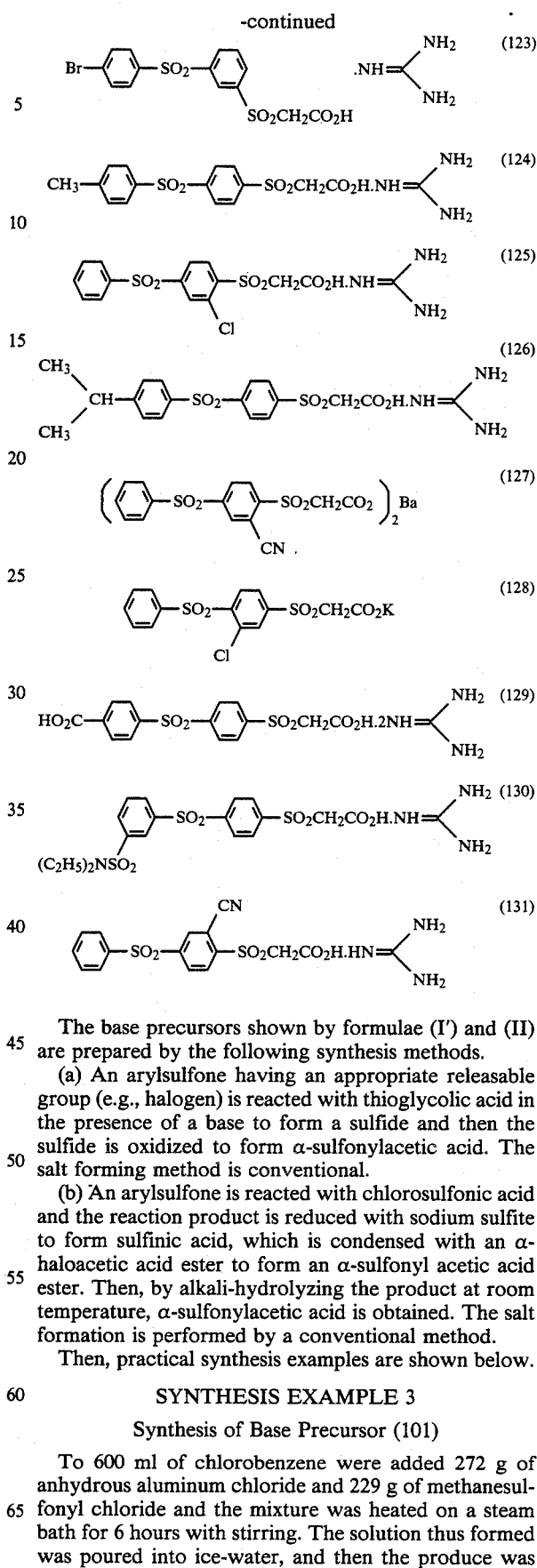

The base precursors shown by formulae (I') and (II) are prepared by the following synthesis methods.

(a) An arylsulfone having an appropriate releasable group (e.g., halogen) is reacted with thioglycolic acid in the presence of a base to form a sulfide and then the sulfide is oxidized to form α-sulfonylacetic acid. The salt forming method is conventional.

(b) An arylsulfone is reacted with chlorosulfonic acid and the reaction product is reduced with sodium sulfite to form sulfinic acid, which is condensed with an α-haloacetic acid ester to form an α-sulfonyl acetic acid ester. Then, by alkali-hydrolyzing the product at room temperature, α-sulfonylacetic acid is obtained. The salt formation is performed by a conventional method.

Then, practical synthesis examples are shown below.

SYNTHESIS EXAMPLE 3

Synthesis of Base Precursor (101)

To 600 ml of chlorobenzene were added 272 g of anhydrous aluminum chloride and 229 g of methanesulfonyl chloride and the mixture was heated on a steam bath for 6 hours with stirring. The solution thus formed was poured into ice-water, and then the produce was extracted with 400 ml of methylene chloride. Methylene chloride was distilled off from the extract under reduced pressure. To the residue thus formed was added 300 ml of methanol, the mixture was cooled to 15° C., and crystals thus deposited were collected by filtration to provide 212 g 1-chloro-4-methylsulfonyl benzene having a melting point of 92° to 94° C.

To 1.6 liters of dimethylformamide were added 144 g of thioglycolic acid (85% in purity) and 532 g of a 28% methanol solution of sodium methoxide to form the disodium salt of thioglycolic acid. To the salt was added 200 g of 1-chloro-4-methylsulfonyl benzene prepared above and while distilling off methanol, the mixture was heated to 100° C. for 6 hours with stirring, whereby a large amount of a white salt deposited. The reaction mixture thus formed was added to an aqueous hydrochloric acid solution and the product thus formed was extracted twice, each time with 400 ml of methylene chloride.

Then, the methylene chloride was distilled off under reduced pressure, and to the residue thus formed were added 270 ml of toluene and 30 ml of ethyl acetate. The reaction mixture was cooled to 5° C. and p-methylsulfonylphenylsulfenylacetic acid thus deposited was collected by filtration. The amount of the product was 120 g and the melting point was 136° to 139° C.

To 600 ml of water were added 120 g of p-methylsulfonylphenylsulfenylacetic acid and 1 g of sodium tungestinate, and then 120 g of 35% hydrogen peroxide was added dropwise thereto at a temperature below 85° C. Furthermore, after stirring the mixture, the reaction mixture was cooled and crystals thus deposited were collected by filtration to provide 130 g of p-methylsulfonylphenylsulfonylacetic acid. The melting point thereof was 191° to 193° C. (decompd.).

To a mixture of 27.8 g of p-methylsulfonylphenylsulfonylacetic acid and 140 ml of methanol was added dropwise with care an aqueous solution of about 9 g of guanidine carbonate to neutralize the compound. Crystals thus formed were collected to provide 29.0 g of Base Precursor (101). The melting point was 246° to 250° C. (decompd.).

SYNTHESIS EXAMPLE 4

Synthesis of Base Precursor (123)

From 200 g of anhydrous aluminum chloride, 153 ml of benzenesulfonyl chloride, 138 ml of bromobenzene, and 600 ml of methylene chloride was prepared 220 g of p-bromophenyl-phenyl-sulfone according to the method of *Journal of Chem. Soc.*, p. 2508 (1960). To 100 ml of chlorosulfonic acid was added 100 g of p-bromophenylphenylsulfone, and after stirring the mixture for 4 hours at 130° to 140° C., the mixture was poured into ice water to provide 121 g of 3-(4-bromophenylsulfonyl)benzenesulfonyl chloride.

To 150 ml of water was added 85 g of sodium sulfite and then 54 g of 3-(4-bromophenylsulfonyl)benzenesulfonyl chloride was added thereto. After stirring the mixture for 2 hours at 50° C., the reaction mixture thus obtained was ice-cooled and crystals thus formed were collected by filtration. To the crystals thus obtained were added 40 ml of water, 40 ml of acetonitrile and 15 ml of methyl chloroacetate followed by refluxing for 2 hours. The reaction mixture thus formed was extracted with chloroform and then chloroform was distilled off from the extract to provide 32.7 g of oily 3-(4-bromophenylsulfonyl)phenylsulfonylacetic acid methyl ester. Then, the oily product thus obtained was added to a mixture of 60 ml of water, 60 ml of methanol, and 8.1 g of potassium hydroxide and the resultant mixture was stirred for one hour at room temperature. After adding 20 ml of 35% hydrochloric acid to the reaction mixture, the mixture was ice-cooled and crystals thus deposited were collected by filtration to provide 25.4 g of 3-(4-bromophenylsulfonyl)phenylsulfonylacetic acid. By neutralizing 21 g of the crystals thus obtained with 4.5 g of guanidine carbonate as in Synthesis Example 3 22.3 g of Base Precursor (123) was obtained. The melting point was 85° C. and the decomposition point was 95° C.

Other base precursors could be also prepared in an analogous manner as above, and the melting points of typical precursors are shown in the following table.

| Base Precursor | Melting point |
| --- | --- |
| (101) | 246–250° C. (decomd.) |
| (102) | 232–236° C. (decomd.) |
| (106) | above 250° C. |
| (108) | 190° C. (decomd.) |
| (109) | 106° C. (decomd.) |
| (111) | 172–175° C. (decomd.) |
| (112) | 91° C. (decomd.) |
| (113) | above 250° C. |
| (115) | 137–139° C. (decomd.) |
| (116) | 132–133° C. (decomd.) |
| (120) | above 250° C. |
| (121) | 152–153° C. (decomd.) |
| (122) | 147–149° C. (decomd.) |
| (123) | 85° C. (decomd. at 95° C.) |
| (124) | 168–170° C. (decomd.) |
| (126) | 175–178° C. |
| (129) | 85–90° C. (decomd.) |
| (130) | 125–128° C. (decomd. at 170° C.) 175–180° C. |

The base precursor used in the present invention can be employed in a wide range of amounts. For example, it is advantageous for the base precursor be used in a coverage from 0.001 to 50% by weight, preferably 0.01 to 40% by weight based on the dry weight of the coating.

The base precursor in the present invention may be used alone or as a mixture of two or more of the base precursors or they may be used in combination with other known base precursor or precursors.

A silver halide light-sensitive material used in the present invention comprises a support having coated thereon at least one silver halide emulsion layer comprising a silver halide dispersed in a binder. The silver halide light-sensitive material may further have at least one of an interlayer, a filter layer, an antihalation layer, a protective layer, and an image fixing (receiving) layer.

In the present invention a heat developable color photographic silver halide material may also be used as a heat developable light-sensitive material.

The base precursors in teh present invention can be incorporated into any of these layers; however, it is preferably incorporated in a silver halide emulsion layer. When the fixing layer is provided on a different support from that on which the silver halide emulsion layer is coated, the base precursor may be incorporated to this fixing layer. In this case a fixing material having a fixing layer and a heat developable light-sensitive material are used in combination.

Examples of silver halide include silver chloride, silver chlorobromide, silver chloroiodide, silver bromide, silver iodobromide, silver chloroiodobromide, silver iodide. An organic silver salt such as silver benzotriazole may also be incorporated to a silver halide emulsion as an oxidizing agent.

The base precursor is incorporated into at least one of the above-described layers by dissolving it into water or a water-miscible organic solvent having a low boiling point (such as methanol, ethanol, acetone, dimethyl formamide, etc.) or a high boiling point (such as those disclosed hereinafter as a solvent for a dye providing material) or into a mixture of such an organic solvent and water, and dissolving or dispersing the thus obtained solution to a coating composition for the layer. The base precursor may also be dispersed in a binder solution directly.

In the present invention a dye-providing material which releases or produces a mobile dye corresponding to or reversely corresponding to a reduction reaction of a silver halide through a reducing agent may also be preferably used. Examples of such materials include coupler, a dye which is able to form positive color images by a photographic silver dye bleaching process, a dye having introduced therein a nitrogen-containing heterocyclic ring group, a dye-providing material which releases a mobile dye by a coupling reaction with a reducing agent which is oxidized by an oxidation reduction reaction with a silver halide or an organic silver salt upon heat development, a non-diffusible image-forming compound which causes self ring closure in the presence of a base to release a diffusible dye, but does not release the dye when the compound reacts with the oxidation product of a developing agnet, a nondiffusible image-forming compound which does not release a dye by itself but releases a dye when the compound reacts with a reducing agent, and a linked donor acceptor compound which is a nondiffusible image-forming compound and causes a donor-acceptor reaction in the presence of a base to release a diffusible dye, but does not substantially release the dye when the compound reacts with the oxidation product of a developing agent.

When an organic silver salt oxidizing agent is present in the reaction system, the foregoing reaction proceeds well and results in a high image density. Accordingly, particularly preferred embodiment in this invention involves an organic silver salt oxidizing agent in the reaction system.

The effect of the base precursor of this invention is particularly remarkable when used together with a light-sensitive silver halide emulsion that has been spectrally sensitized. That is, when the precursor is used together with a spectrally sensitized light-sensitive silver halide emulsion, the extent of increasing the image density is particularly high.

The spectral sensitization of silver halide emulsions is performed using methine dyes, etc. Examples of dyes useful for spectral sensitization include cyanine dyes, mercoyanine dyes, complex cyanine dyes, complex merocyanine dyes, holopolar cyanine dyes, hemicyanine dyes, styryl dyes, and hemioxonole dyes. Particularly useful dyes are cyanine dyes, merocyanine dyes, and complex merocyanine dyes. For these dyes, nuclei usually utilized for cyanine dyes can be applied as basic heterocyclic ring nuclei. For example, there are pyrroline nuclei, oxazoline nuclei, thiazoline nuclei, pyrrole nuclei, oxazole nuclei, thiazole nuclei, selenazole nuclei, imidazole nuclei, tetrazole nuclei, pyridine nuclei, etc.; the nuclei formed by the fusion of aliphatic hydrocarbon rings to the foregoing nuclei and the nuclei formed by the fusion of aromatic hydrocarbon rings to the foregoing nuclei, such as indolenine nuclei, benzindolenine nuclei, indole nuclei, benzoxazole nuclei, naphthoxazole nuclei, benzothiazole nuclei, naphthothiazole nuclei, benzoselenazole nuclei, benzimidazole nuclei, quinoline nuclei, etc. These nuclei may be substituted on carbon atoms.

For the merocyanine dye or complex merocyanine dye can be applied a 5- or 6-membered heterocyclic nucleus such as a pyrazolin-5-one nucleus, thiohydantoin nucleus, a 2-thiooxazolidine-2,4-dione nucleus, a thiazolidine-2,4-dione nucleus, a rhodanine nucleus, a thiobarbituric acid nucleus, etc., as a nucleus having a ketomethylene structure.

These sensitizing dyes may be used individually or as a combination thereof. A combination of sensitizing dyes is frequently used for supersensitization. Examples of useful sensitizing dyes are described in, for example, German Pat. No. 929,080; U.S. Pat. Nos. 2,493,748; 2,503,776; 2,519,001; 2,912,329; 3,656,959; 3,672,897; 3,694,217; 4,025,349; 4,046,572; U.K. Pat. No. 1,242,588; Japanese Patent Publication Nos. 14,030/'69 and 24,844/'77.

The amount of the sensitizing dye is from 0.001 g to 20 g, and preferably from 0.01 g to 2 g per 100 g of silver of the silver halide emulsion.

In this invention, silver may be used as the image-forming material or various image-forming materials (preferably, a dye-providing material) may be used in various manners.

Examples of the dye-providing material include the followings; Couplers which form color images by combining with the oxidation product of a developing agent which is conventionally used for liquid development can be used as the image-forming materials in this invention. This includes 5-pyrazolone couplers, pyrazolobenzimidazole couplers, cyanoacetylcumarone couplers, open chain acylacetonitrile couplers, etc., as magenta couplers; acylacetamido couplers (e.g., benzoylacetanilides, pyvaloylacetanilides, etc.), etc. as yellow couplers; and naphthol couplers, phenol couplers, etc., as cyan couplers. Non-diffusible couplers having a hydrophobic group, a so-called ballast group, in the molecule, or polymerized couplers are preferred. The couplers may be four equivalent or two equivalent to. silver. Also, the couplers may be colored couplers having a color correction effect or so-called DIR couplers capable of releasing a development inhibitor with the progress of development.

Also, dyes forming positive color images by a photographic silver dye bleaching process, for example, the dyes described in *Research Disclosure*, April 1976, pages 30-32 (RD-14433), ibid., December 1976, pages 14-15 (RD-15227), U.S. Pat. No. 4,235,957 and the leuco dyes described in U.S. Pat. Nos. 3,985,565; 4,022,617, etc.

Also, the dyes having introduced therein a nitrogen-containing heterocyclic ring group described in *Research Disclosure*, May 1978, pages 54-58, (RD-16966) can be used.

Furthermore, a dye-providing materials releasing a mobile dye by utilizing a coupling reaction with a reducing agent oxidized by an oxidation reduction reaction with silver halide or an organic silver salt upon heat development at high temperature described in European Patent Application (published) Nos. 79,056 and 67,455; West German Pat. No. 3,217,853, etc., and a dye-providing materials releasing a mobile dye as the result of an oxidation-reduction reaction with silver halide or an organic silver salt upon heat development at a high temperature described in European Patent Application (published) Nos. 76,492, 66,282, 120,306 and 119,470; West German Pat. No. 3,215,485, can be used.

The dye-providing material used in this invention are preferably shown by following formula (CI)

$$(Dye-X)_q-Y \tag{CI}$$

wherein Dye represents a dye which becomes a mobile dye when released from the molecule and has, preferably, a hydrophilic group. As such dyes, there are an azo dye, an azomethine dye, an anthraquinone dye, a naphthoquinone dye, a styryl dye, a nitro dye, a quinoline dye, a carbonyl dye, a phthalocyanine dye, etc., and specific examples of them are shown below. In addition, these dyes can be used as the form of having their absorption temporarily shifted to a short wavelength side, which can recover the original color by development.

For example, the dyes described in European Patent Application (published) No. 76,492 can be thus utilized.

X in the aforesaid formula represents a simple bond or a linkage group, such as, for example, —NR— group (wherein R represents a hydrogen atom, an alkyl group or a substituted alkyl group), —SO$_2$— group, —CO— group, an alkylene group, a substituted alkylene group, a phenylene group, a substituted phenylene group, a naphthylene group, a substituted naphthylene group, —O— group, —SO— group, or a group formed by the combination of two or more above-described groups.

Y in the above formula represents a group having a property of releasing Dye in direct or inverse proportion to a light-sensitive silver salt having imagewise latent images to form a difference in diffusibility between the released dye and the compound shown by Dye-X-Y.

In the formula (CI) q represents 1 or 2, and when q is 2, Dye-X may be the same or different.

The group represented by Y is now explained in detail.

Y in formula (CI) described above is selected so that the compound represented by formula (CI) becomes a non-diffusible image-forming compound which is oxidized and self-cleaved as result of development to provide a diffusible dye.

An example of Y effective for this type of compound is an N-substituted sulfamoyl group. An example of Y is a group represented by formula (CII)

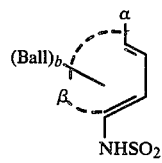

(CII)

wherein, $\beta$ represents a nonmetallic atomic group necessary for forming a benzene ring, said benzene ring may be condensed with a carbon ring or a heterocyclic ring to form, for example, a naphthalene ring, a quinoline ring, a 5,6,7,8-tetrahydronaphthalene ring, a chroman ring, etc.

$\alpha$ in formula (CII) represents a group represented —OG$^{11}$ or —NHG$^{12}$ (wherein G$^{11}$ represents a hydrogen atom or a group forming a hydroxy group by hydrolysis and G$^{12}$ represents a hydrogen atom, an alkyl group having from 1 to 22 carbon atoms, or a hydrolyzable group, and Ball represents a ballast group, and b represents 0.1 or 2.

Practical examples of Y are described in Japanese Patent Application (OPI) Nos. 33,826/'73 and 50,736/'78.

Another example of Y suitable for the compound of this type is the group represented by formula (CIII)

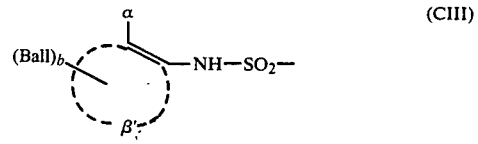

wherein Ball, $\alpha$, and b have the same meaning as in the case of formula (CII) and $\beta'$ represents an atomic group necessary for forming a carbocyclic ring, such as a benzene ring, and said benzene ring may be condensed with a carbon ring or a heterocyclic ring to form a naphthalene ring, a quinoline ring, a 5,6,7,8-tetrahydronaphthalene ring, a chroman ring, etc. Practical examples of Y of this type are described in Japanese Patent Application (OPI) Nos. 113,624/'76; 12,642/'81; 16,130/'81; 16,131/'81; 4043/'82; 650/'82 and U.S. Pat. No. 4,053,312.

Furthermore, still other example of Y suitable for the compound of this type is the group represented by formula (CIV)

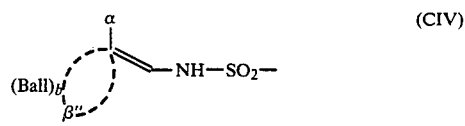

wherein Ball, $\alpha$, and b have the same meaning as in the case of formula (CIII) and $\beta''$ represents an atomic group forming a heterocyclic ring such as a pyrozole ring, a pyridine ring, etc., said heterocyclic ring may be condensed with a carbon ring or a heterocyclic ring. Practical examples of Y of this type are described in Japanese Patent Application (OPI) No. 104,343/'76.

Furthermore, other example of Y suitable for the compound of this type is the group represented by formula (CV)

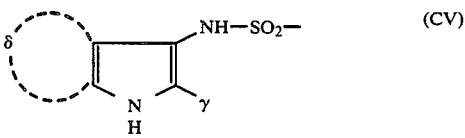

wherein $\gamma$ preferably represents a hydrogen atom, an substituted or unsubstituted alkyl group, a substituted or unsubstituted aryl group, a substituted or unsubstituted heterocyclic ring group, or —CO—G$^{21}$ (wherein G$^{21}$ represents —OG$^{22}$, —S—G$^{22}$, or

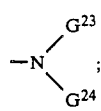

wherein G$^{22}$ represents a hydrogen atom, an alkyl group, a cycloalkyl group, or an aryl group; G$^{23}$ represents a hydrogen atom, an alkyl group, a cycloalkyl group, an aryl group, or an acyl group induced from an aliphatic carboxylic acid, an aromatic carboxylic acid or sulfonic acid; and $G^{24}$ represents a hydrogen atom or an unsubstituted or substituted alkyl group); and δ represents a residue completing a condensed benzene ring.

Practical examples of Y of this kind are described in Japanese Patent Application (OPI) Nos. 104,343/'76; 46,730/'78; 130,122/'79; 85,055/'82, etc.

Moreover, as Y suitable for the compound of this type, there is the group represented by formula (CVI)

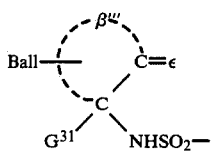
(CVI)

wherein Ball is same as the case of formula (CII); ε represents an oxygen atom or $=NG^{32}$ group (wherein $G^{32}$ represents a hydroxy group or an amino group which may have a substituent); in this case, examples of the compound $H_2N$—$G^{32}$ from which the $=NG^{32}$ group is derived include hydroxylamine, hydrazines, semicarbazides, thiosemicarbazides, etc.; β''' represents an atomic group forming a 5-membered, 6-membered or 7-membered saturated or unsaturated non-aromatic hydrocarbon ring; and $G^{31}$ represents a hydrogen atom or a halogen atom such as fluorine, chlorine, bromine, etc. Practical examples of Y of this kind are described in Japanese Patent Application (OPI) Nos. 3819/'78; 48,534/'79, etc.

Examples of Y of the compound of this type include groups as described, for example, in Japanese Patent Publication Nos. 32,129/'73 and 39,165/'73; Japanese Patent Application (OPI) No. 64,436/'74; U.S. Pat. No. 3,443,934, etc.

As still another example of Y, there is the group represented by formula (CVII)

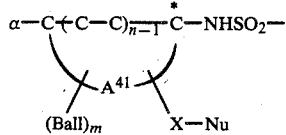
(CVII)

wherein α represents $OR^{41}$ or $NHR^{42}$ (wherein $R^{41}$ represents a hydrogen atom or a hydrolyzable moiety and $R^{42}$ represents a hydrogen atom or an alkyl group having from 1 to 50 carbon atoms); $A^{41}$ represents an atomic group necessary for forming an aromatic ring; Ball represents an organic immobilizing group disposed on an aromatic ring; m represents an integer of 1 or 2; when m is 2, said Ball groups may be the same or different; X represents a divalent organic group having from 1 to 8 carbon atoms and forms a 5- to 12-membered ring with a nucleophilic group (Nu) and an electrophilic center (the carbon atom with *) formed by oxidation; Nu represents a nucleophilic group; n represents an integer of 1 or 2; and α is the same as in the case of above formula (CII). Practical examples of Y of this kind are described in Japanese Patent Application (OPI) No. 20735/'82.

Furthermore, as other type of the compound shown by formula (CI), ther is a nondiffusible image-forming compound which causes self ring closure in the presence of a base to release a diffusible dye, but substantially does not release the dye when the compound reacts with the oxidation product of a developing agent.

Examples of Y effective as a compound of this type include groups represented by formula (CVIII)

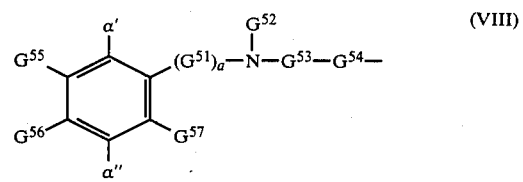
(VIII)

wherein α' represents an oxidizable nucleophilic group such as a hydroxy group, a primary or secondary amino group, a hydroxyamino group, a sulfonamido group, etc., or a precursor thereof; α" represents a dialkylamino group or an optional group defined in regard to α'; $G^{51}$ represents an alkylene group having from 1 to 3 carbon atoms, a represents 0 or 1, $G^{52}$ represents a substituted or unsubstituted alkyl group having from 1 to 40 carbon atoms or a substituted or unsubstituted aryl group having from 6 to 40 carbon atoms, $G^{53}$ represents an electrophilic group such as —CO—, —CS—, etc.; and $G^{54}$ represents an oxygen atom, a sulfur atom, a selenium atom, a nitrogen atom, etc., and when $G^{54}$ is a nitrogen atom, it may be substituted by a hydrogen atom, a substituted or unsubstituted alkyl group having from 1 to 10 carbon atoms, or an aromatic residue having 6 to 20 carbon atoms, $G^{55}$, $G^{56}$ and $G^{57}$ each represents a hydrogen atom, a halogen atom, a group containing a carbonyl group (e.g., an amide group and —COOH), a sulfamoyl group a sulfonamide group, an alkyloxy group having from 1 to 40 carbon atoms or represents the same group as defined for $G^{52}$, $G^{55}$ and $G^{56}$ together may form a ring, or $G^{56}$ may be

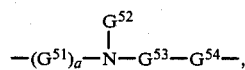

wherein at least one of $G^{52}$, $G^{55}$, $G^{56}$ and $G^{57}$ represents a ballast group. Examples of Y of the compound of this type include groups as described, for example, in Japanese Patent Application (OPI) No. 63,618/'76.

Examples of Y suitable for the compound of this type include groups represented by formulae (CIX) and (CX):

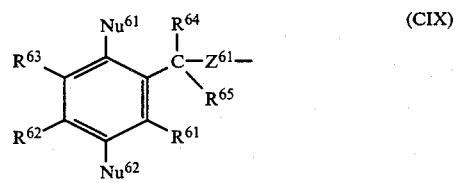
(CIX)

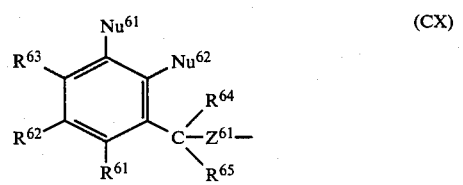
(CX)

wherein $Nu^{61}$ and $Nu^{62}$ (which may be the same or different) each represents a nucleophilic group or a precursor thereof; $Z^{61}$ represents a divalent atomic group which is electrically negative to the carbon atom to which $R^{64}$ and $R^{65}$ are substituted; $R^{61}$, $R^{62}$, and $R^{63}$ each represents a hydrogen atom, a halogen atom, and alkyl group, an alkoxy group, or an acylamino group; when said $R^{61}$ and $R^{62}$ are adjacently disposed on a ring, they may form a condensed ring with the remaining molecule, or said $R^{62}$ and $R^{63}$ may form a condensed ring with the remaining part of the molecule; $R^{64}$ and $R^{65}$ (which may be the same or different) each represents a hydrogen atom, a hydrocarbon group or a substituted hydrocarbon group; and a sufficiently large ballast group, Ball exists at least on the substituent $R^{61}$, $R^{62}$, $R^{63}$, $R^{64}$, or $R^{65}$ for making immobile the aforesaid compound. Practical examples of Y of this kind are described in Japanese Patent Application (OPI) Nos. 69,033/'78 and 130,927/'79.

Also, another Y suitable for the compound of this type, is the group represented by formula (CXI)

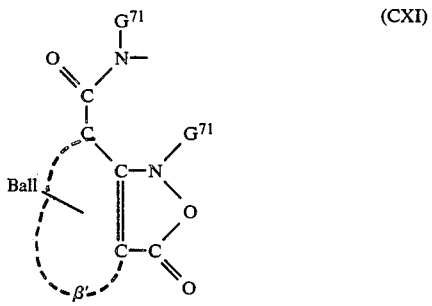

wherein Ball and $\beta'$ are same as defined in formula (CIII); $G^{71}$ represents an alkyl group or a substituted alkyl group. Practical examples of Y of this kind are described in Japanese Patent Application (OPI) Nos. 111,628/'74 and 4,819/'77.

Moreover, another example of the compound shown by formula (CI) above is a non-diffusible image-forming compound which does not release a dye by itself, but releases a dye when the compound reacts with a reducing agent. In this case, it is preferred to use a compound mediating the redox reaction (a so-called electron donor) together with the image-forming compound.

As an example of Y effective for the compound of this type, there is a group shown by formula (CXII)

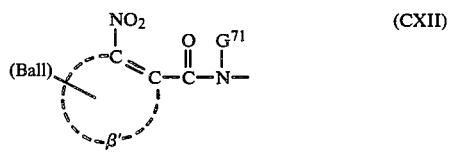

wherein Ball and $\beta'$ are same as defined in formula (CIII) and $G^{71}$ represents an alkyl group or a substituted alkyl group. Practical examples of Y of this kind are described in Japanese Patent Application (OPI) Nos. 35,533/'78 and 110,827/'78.

As still other example of Y suitable for the compound of this type, there is the group shown by formula (CXIII)

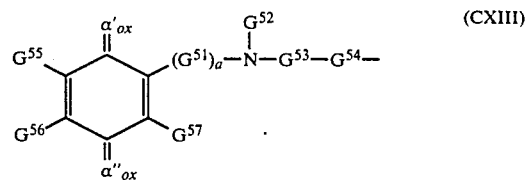

wherein $\alpha'_{ox}$ and $\alpha''_{ox}$ each represents a group giving $\alpha'$ or $\alpha''$ by reduction and $\alpha'$, $\alpha''$, $G^{51}$, $G^{52}$, $G^{53}$, $G^{54}$, $G^{55}$, $G^{56}$, $G^{57}$, and a are same as the case of formula (CVIII). Practical examples of Y of this kind are described in Japanese Patent Application (OPI) NO. 110,827/'78 and U.S. Pat. Nos. 4,356,249 and 4,358,525.

Other examples of Y suitable for the compound of this type include groups represented by formulae (CXIV A) and (CXIV B)

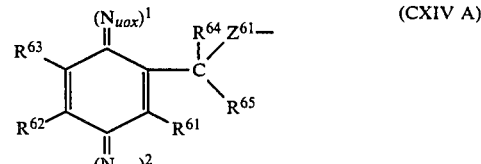

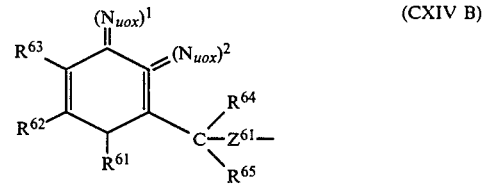

wherein $(N_{uox})^1$ and $(N_{uox})^2$, which may be the same or different, each represents an oxidized nucleopholic group and other symbols are the same as in the cases of formulae (CIX) and (CX). Practical examples of Y of this kind are described in Japanese Patent Application (OPI) Nos. 130,927/'79 and 164,342/'81.

In the patent specifications cited in regard to formulae (CXII), (CXIII), (CXIV A) and (CXIV B), electron donors which can be used with the aforesaid compounds are described.

Also, as other type of compound shown by general formula (CI), there is further a linked donor acceptor compound (LDA compound). This compound is a non-diffusible image-forming compound which causes a donor-acceptor reaction in the presence of a base to release a diffusible dye, but does not substantially release the dye when the compound reacts with the oxidation product of a developing agent.

Example of Y effective for the compound of this type, there is, for example, the group shown by following formula (CXV). Practical examples of Y of this kind are described in British Patent Application (published) No. 2,140,927.

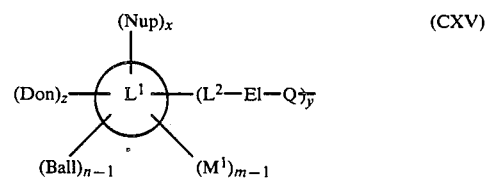

wherein n, x, y, and z are 1 or 2; m represents an integer of 1 or more; Don represents a group containing an electron donor or a precursor moiety thereof; $L^1$ represents an organic group connecting Nup and —$L^2$—$E^1$—Q or Don; Nup represents a precursor for a nucleophilic group; $E^1$ represents an electrophilic center; Q represents a divalent group; Ball represents a ballast group; $L^2$ represents a linkage group and $M^1$ represents an optional substituent.

The ballast group is an organic ballast group capable of rendering the dye image-forming compound nondiffusible, and it is preferred that the ballast group is a group containing a hydrophobic group having from 8 to 32 carbon atoms. Such an organic ballast group is bonded to the dye image-forming compound directly or through a linkage group (e.g., an imino bond, an ether bond, a thioether bond, a carbonamido bond, a sulfonamido bond, a ureido bond, an ester bond, an imido bond, a carbamoyl bond, a sulfamoyl bond, etc., either singly or as a combination thereof.

The dye releasing or providing material which releases a hydrophilic diffusible dye which can be preferably used in the present invention is a compound described in European Patent Application (OPI) No. 76,492, which disclosure is herein incorporated by reference, as a dye releasing compound and is represented by the following general formula:

$$R_a-SO_2-D \quad (DR)$$

wherein $R_a$ represents a reducing group capable of being oxidized by the silver halide; and D represents an image forming dye moiety containing a hydrophilic group.

The above-described compound is oxidized coresponding to or in a reverse manner corresponding to the latent image distributed imagewise in the silver halide and a mobile dye is released in an imagewise manner.

Detailed definitions of $R_a$ and D, examples of the specific compounds and synthesis examples thereof are described in European Patent Application (OPI) No. 76,492.

Suitable dye releasing redox compounds which also can be used in the present invention include the compounds as described, for example, in U.S. Pat. No. 4,055,428, Japanese Patent Application (OPI) Nos. 12642/81, 16130/81, 16131/81, 650/82 and 4043/82, U.S. Pat. Nos. 3,928,312 and 4,076,529, U.S. Published Patent Application B 351,673, U.S. Pat. Nos. 4,135,929 and 4,198,235, Japanese Patent Application (OPI) No. 46730/78, U.S. Pat. Nos. 4,273,855, 4,149,892, 4,142,891 and 4,258,120, etc., the disclosures of which are incorporated herein by reference. These compounds are also effective in addition to the above-described compounds.

Further, the dye releasing redox compounds which release a yellow dye as described, for example, in U.S. Pat. Nos. 4,013,633, 4,156,609, 4,148,641, 4,165,987, 4,148,643, 4,183,755, 4,246,414, 4,268,625 and 4,245,023, Japanese Patent Application (OPI) Nos. 71072/81, 25737/81, 138744/80, 134849/80, 106727/77, 114930/76, etc., the disclosures of which are herein incorporated by reference, can be effectively used in the present invention.

The dye releasing redox compounds which release a magenta dye as described, for example, in U.S. Pat. Nos. 3,954,476, 3,932,380, 3,931,144, 3,932,381, 4,268,624 and 4,255,509, Japanese Patent Application (OPI) Nos. 73057/81, 71060/81, 134850/80, 40402/80, 36804/80, 23628/78, 106727/77, 33142/80 and 53329/80, etc., the disclosure of which are herein incorporated by reference, can be effectively used in the present invention.

The dye releasing redox compounds which release a cyan dye as described, for example, in U.S. Pat. Nos. 3,929,760, 4,013,635, 3,942,987, 4,273,708, 4,148,642, 4,183,754, 4,147,544, 4,165,238, 4,246,414 and 4,268,625, Japanese Patent Application (OPI) Nos. 71061/81, 47823/78, 8827/77 and 143323/78, etc., the disclosures of which are herein incorporated by reference, can be effectively used in the present invention.

The dye-providing materials may be used solely or a combination of two or more. In the case of using a mixture, the same color may be formed by using two or more dyes, or black may be formed using two or more dyes.

Practical examples of the image-forming material for use in this invention are described in the patent specifications indicated above. Example compounds are shown below.

For example, the dye-providing materials shown by foregoing formula (CI) are as follows.

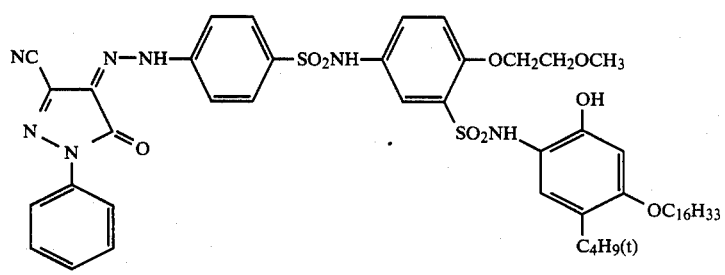

(1)

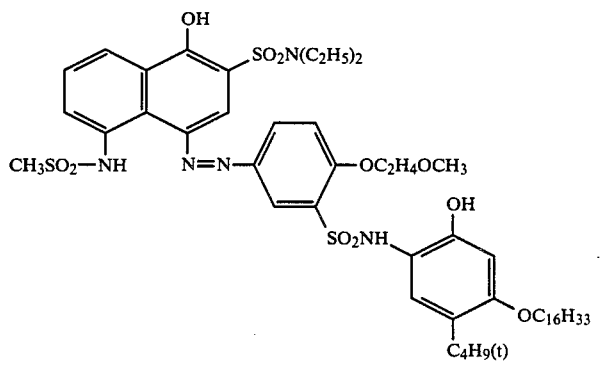
(2)
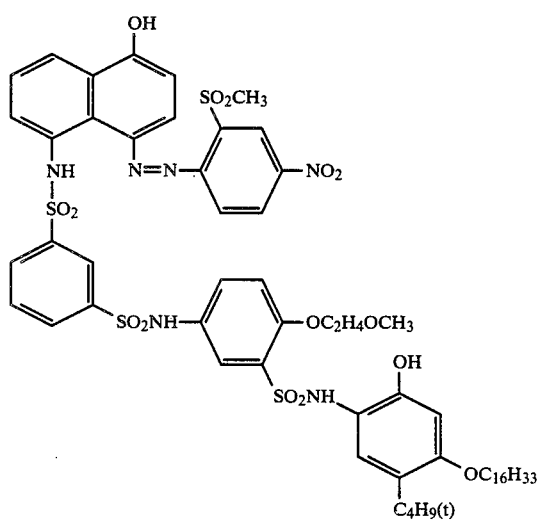
(3)
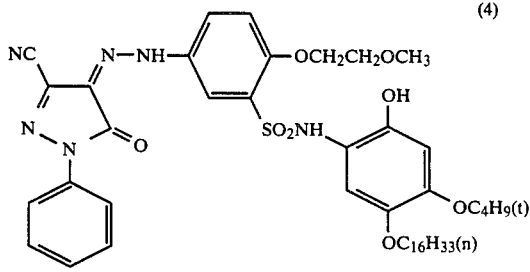
(4)
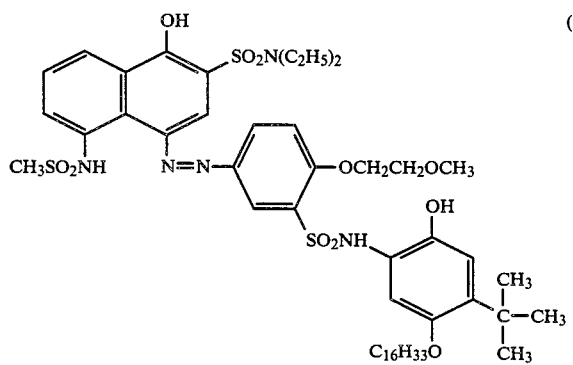
(5)
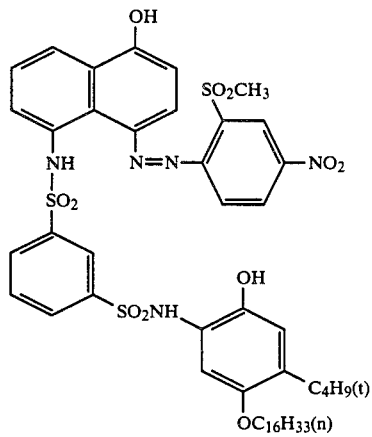
(6)
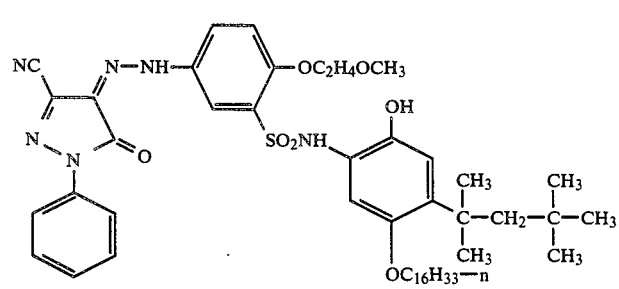
(7)

-continued
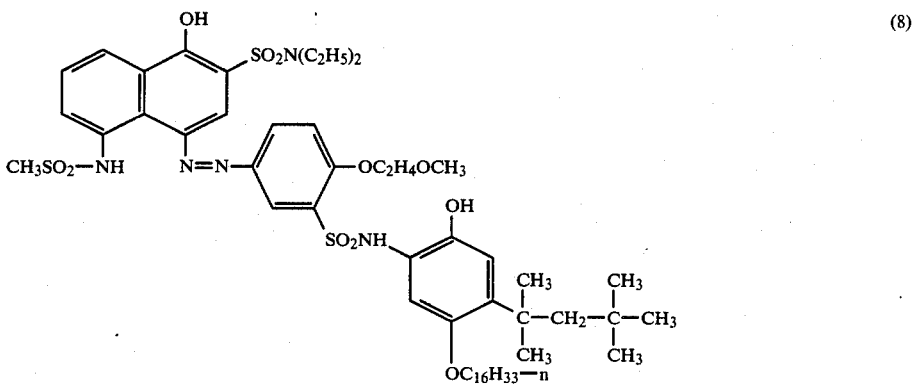
(8)
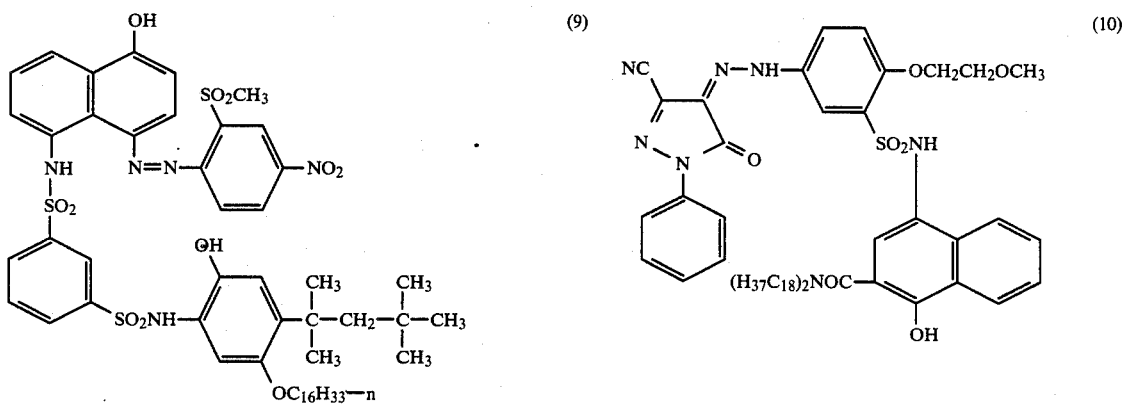
(9) (10)
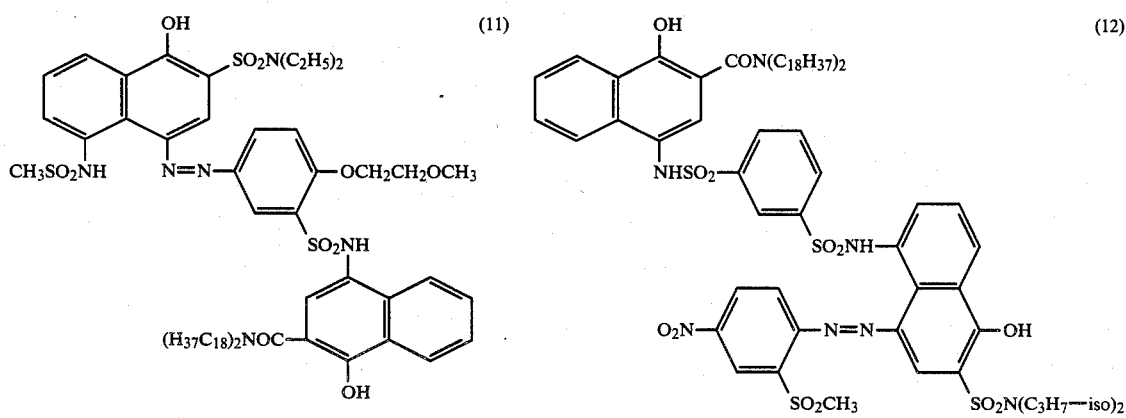
(11) (12)
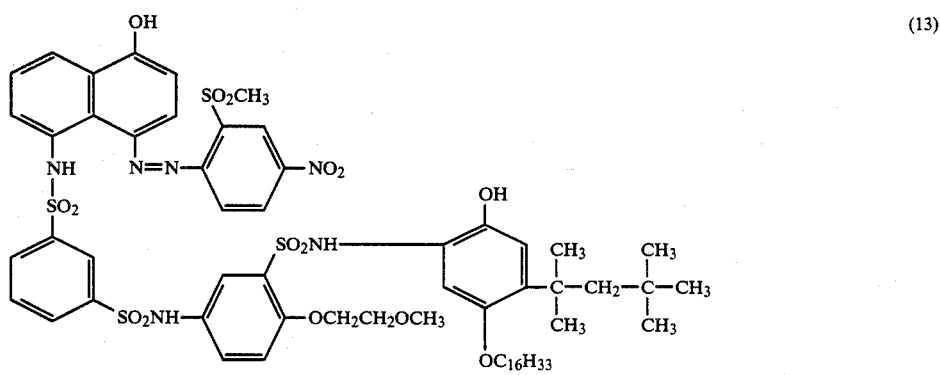
(13)

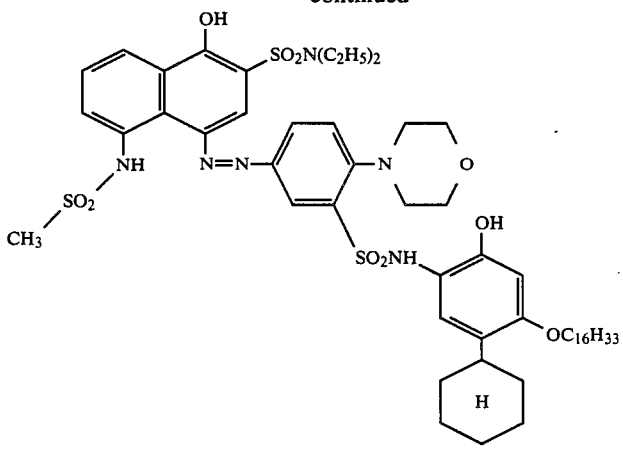

(14)

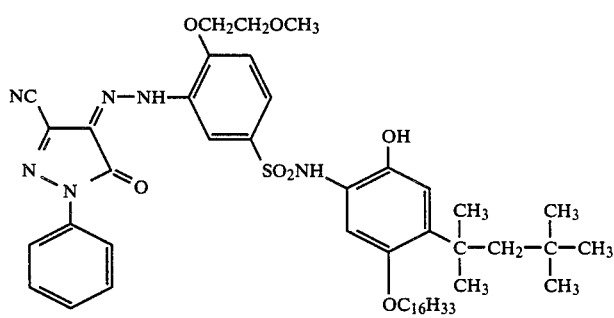

(15)

The above-described specific compounds are illustrated as non-limiting examples of the dye-providing materials for use in this invention.

In the present invention a dye-providing material which releases or produces a mobile dye corresponding to or reversely corresponding to a reduction reaction of a silver halide through a reducing agent may also be preferably used. Examples of such materials include coupler, a dye which is able to form positive color images by a photographic silver dye bleaching process, a dye having introduced therein a nitrogen-containing heterocyclic ring group, a dye-providing material which releases a mobile dye by a coupling reaction with a reducing agent which is oxidized by an oxidation reduction reaction with a silver halide or an organic silver salt upon heat development, a non-diffusible image-forming compound which causes self ring closure in the presence of a base to release a diffusible dye, but does not release the dye when the compound reacts with the oxidation product of a developing agnet, a non-diffusible image-forming compound which does not release a dye by itself but releases a dye when the compound reacts with a reducing agent, and a linked donor acceptor compound which is a nondiffusible image-forming compound and causes a donor-acceptor reaction in the presence of a base to release a diffusible dye, but does not substantially release the dye when the compound reacts with the oxidation product of a developing agent.

Many of the above-described materials form an imagewise distribution of a mobile dye by heat development corresponding to the exposed portion of a light-sensitive material, and a process for visualizing the dye image in a dye-fixing material (so-called diffusion transfer process) is described in the above-indicated patent specifications and European Patent Application (published) No. 119,615.

In the present invention, the dye providing material and other photographic additives may be introduced to the layer of the light sensitive material according on the method disclosed in column 13 of U.S. Pat. No. 4,500,627.

In the present invention, developing agents and reducing agents as disclosed in column 49 of U.S. Pat. No. 4,500,626 may be used.

In the present invention, silver halide and organic silver compounds as disclosed in columns 14–15 in U.S. Pat. No. 4,500,627 may be used. Binders which are disclosed in column 15 of the same patent may also be used in the present invention.

When spectral sensitization is carried out in the present invention sensitizing dyes disclosed in columns 15–16 of U.S. Pat. No. 4,500,627 may be used in the manner according on the method disclosed therein.

Methods for exposure, development and aftertreatment disclosed in column 20 of U.S. Pat. No. 4,500,627 may be applied to the heat developabe light-sensitive material of the present invention.

Supports, surfactants, hardening agents, mordants, dye transfer assistants, dye fixing layers, dye fixing materials, etc., which are disclosed in U.S. Pat. No. 4,500,627 may be used in the present invention.

The disclosures of U.S. Pat. Nos. 4,500,626 and 4,500,627, and European Patent Application (published) No. 119,615 supra are hereby incorporated by reference.

The dye releasing or dye providing material is suitably used in a range from about 10 mg/m$^2$ to about 15 mg/m$^2$ and preferably in a range from mg/m$^2$ to 10 mg/m$^2$ in a total.

The dye releasing or providing material of the formula (CI) used in the present invention can be introduced into a layer of the light-sensitive material using known methods such as method as described in U.S. Pat. No. 2,322,027. In this case, an organic solvent having a high boiling point an organic solvent having a low boiling point as described below can be used. For example, the dye releasing material can be dispersed in a hydrophilic colloid after it is dissolved in an organic solvent having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctylbutyl phosphate, etc.), a citric acid ester (for example, tributyl acetylcitrate, etc.), a benzoic acid ester (for example, octyl benzoate, etc.), an alkylamide (for example, diethyl laurylamide, etc.), an aliphatic acid ester (for example, dibutoxyethyl succinate, dioctyl azelate, etc.), a trimesic acid ester (for example, tributyl trimesate, etc.), etc., or an organic solvent having a low boiling point of about 30° to 160° C., for example, a lower alkyl acetate such as ethyl acetate, butyl acetate, etc., ethyl priopionate, secondary butyl alcohol, methyl isobutyl ketone, $\beta$-ethoxyethyl acetate, methyl cellosolve acetate, cyclohexanone, etc. The above-described organic solvents having a high boiling point and organic solvents having a low boiling point may be used as a mixture thereof, if desired.

Further, it is possible to use a dispersion method employing a polymer as described in Japanese Patent Publication No. 39853/76 and Japanese Patent Application (OPI) No. 59943/76. Moreover, various surface active agents can be used when the dye releasing redox compound is dispersed in a hydrophilic colloid. For this purpose, the surface active agents illustrated hereinafter in the specification can be used.

In the present invention, if desired, a reducing agent may also be used. The reducing agent in this case is so-called auxiliary.

Various combinations of developing agents as described in U.S. Pat. No. 3,039,869 can also be used.

In the present invention, the amount of the reducing agent which can be employed is from 0.01 mol to 20 mols per mol of silver and more preferably from 0.1 mol to 10 mols per mol of silver.

In the embodiment of the present invention in which the organic silver salt oxidizing agent is not used together with but the silver halide is used alone, particularly preferred silver halide is silver halide partially containing a silver iodide crystal in the particles. That is, a silver halide in which the X-ray diffraction pattern shows that of pure silver iodide is particularly preferred.

In photographic materials a silver halide containing two or more kinds of halogen atoms can be used. Such a silver halide yields a completely mixed crystal in a conventional silver halide emulsion. For example, the particles of silver iodobromide show an X-ray diffraction pattern at a position corresponding to the mixed ratio of silver iodide crystal and silver bromide crystal but not at a position corresponding to pure silver iodide crystal and pure silver bromide crystal separately.

Particularly preferred examples of silver halides which can be used in the present invention include silver chloroiodide, silver iodobromide, and silver chloroiodobromide each containing silver iodide crystals in the particles thereof and showing X-ray diffraction pattern of silver iodide crystals.

The process for preparing those silver halides using silver iodobromide as exemplary. That is, silver iodobromide is prepared by first adding a silver nitrate solution to a potassium bromide solution to form silver bromide particles and then adding potassium iodide to the mixture.

Two or more kinds of silver halides in which the particle size and/or a halogen composition are different from each other may be used in admixture, if desired.

The average particle size of the silver halide used in the present invention is preferably from about 0.001 $\mu$m to about 10 $\mu$m and more preferably from 0.001 $\mu$m to 5 $\mu$m.

The silver halide used in the present invention may be used as is. However, the silver halide may also be chemically sensitized with a chemical sensitizing agent such as compounds of sulfur, selenium or tellurium, etc., or compounds of gold, platinum, palladium, rhodium or iridium, etc., a reducing agent such as tin halide, etc., or a combination thereof. The details thereof are described in T. H. James, *The Theory of the Photographic Process*, the Fourth Edition, Chapter 5, pages 149 to 169.

In a particularly preferred embodiment of the present invention, an organic silver salt oxidizing agent is also used. The organic silver salt oxidizing agent is a silver salt which forms a silver image upon reaction with the above-described image forming substance or a reducing agent which are copresent, if desired, with the image forming substance, when it is heated to a temperature of above about 80° C. and, preferably, above 100° C. in the presence of exposed silver halide. Due to the copresence of the organic silver salt oxidizing agent, a light-sensitive material which provides higher color density can be obtained.

The silver halide used in this case need not always have the characteristic that the silver halide contains pure silver iodide crystals in the case of using the silver halide alone. Any silver halide which is known in the art can be used.

Examples of such organic silver salt oxidizing agents include those described in European Patent Application (OPI) No. 76,492.

A silver salt of an organic compound having a carboxy group can be used. Typical examples thereof include a silver salt of an aliphatic carboxylic acid and a silver salt of an aromatic carboxylic acid.

In addition, a silver salt of a compound containing a mercapto group or a thione group and a derivative thereof can be used.

Further, a silver salt of a compound containing an imino group can be employed. Suitable examples of these compounds include a silver salt of benzotriazole and the derivatives thereof as described in Japanese Patent Publication Nos. 30270/69 and 18416/70, for example, a silver salt of benzotriazole, a silver salt of alkyl-substituted benzotriazole such as a silver salt of methylbenzotriazole, etc., a silver salt of a halogen-substituted benzotriazole such as a silver salt of 5-chlorobenzotriazole, etc., a silver salt of carboimidobenzotriazole such as a silver salt of butylcarboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, a silver salt as described in *Research Disclosure*, Vol. 170, No. 17029 (June, 1978) and an organic metal salt such as copper stearate, etc., are organic metal salt oxidizing agents capable of being used in the present invention.

Methods of preparing these silver halide and organic silver salt oxidizing agents and techniques of blending them are described in *Research Disclosure*, No. 17029, Japanese Patent Application (OPI) Nos. 32928/75 and 42529/76, U.S. Pat. No. 3,700,458, and Japanese Patent Application (OPI) Nos. 13224/74 and 17216/75.

A suitable coating amount of the light-sensitive silver halide and the organic silver salt oxidizing agent employed in the present invention is in a total of from 50 mg/m$^2$ to 10 g/m$^2$ calculated as silver.

The light-sensitive silver halide and the organic silver salt oxidizing agent used in the present invention are prepared in the binder as described below. Further, the dye releasing redox compound used in the present invention is dispersed in the binder described below.

The binder which can be used in the present invention can be employed alone or as a combination thereof. A hydrophilic binder can be used as the binder according to the present invention. Typical hydrophilic binders are transparent or translucent hydrophilic colloids, examples of which include natural substances, for example, a protein such as gelatin, a gelatin derivative, a cellulose derivative, etc., a polysaccharide such as starch, gum arabic, etc., and a synthetic polymer, for example, a water-soluble polyvinyl compound such as polyvinyl alcohol, polyvinyl pyrrolidone, acrylamide polymer, etc. Another example of a synthetic polymer compound is a dispersed vinyl compound in a latex form which is used for the purpose of increasing the dimensional stability of the photographic material.

Suitable supports used in the light-sensitive material and the dye fixing material employed, if desired, according to the present invention are supports which can endure the processing temperature. As ordinary support, such as glass, paper, metal or analogues thereof may be used, but also an acetyl cellulose film, a cellulose ester film, a polyvinyl acetal film, a polystyrene film, a polycarbonate film, a polyethylene terephthalate film, and a film related thereto or a synthetic resin material may be used. Further, a paper support laminated with a polymer such as polyethylene, etc., can be used. The polyesters described in U.S. Pat. Nos. 3,634,089 and 3,725,070 are preferably used.

In the present invention, various kinds of dye releasing activators can be used. A dye releasing activator is a substance which accelerates the ocidation-reduction reaction between the light-sensitive silver halide and/or the organic silver salt oxidizing agent and dye releasing redox compound or accelerates release of a dye to its nucleophilic action on the ozidized dye releasing redox compound in the dye releasing reaction which subsequently occurs, and a base and a base precursor can be used. It is particularly advantageous to use dye releasing activators in order to accelerate the reactions in the present invention.

Examples of preferred bases are amines which include trialkylamines, hydroxylamines, aliphatic polyamines, N-alkyl substituted aromatic amines, N-hydroxyalkyl substituted aromatic amines and bis[p-(dialkylamino)phenyl]methanes. Further, betaine tetramethylammonium iodide and diaminobutane dihydrochloride as described in U.S. Pat. No. 2,410,644, and urea and organic compounds including amino acids such as 6-aminocaproic acid as described in U.S. Pat. No. 3,506,444 can be used. A base precursor is a substance which releases a basic component upon heating. Examples of typical base precursors are described in British Pat. No. 998,949. A preferred base precursor is a salt of a carboxylic acid and an organic base, and examples of suitable carboxylic acids include trichloroacetic acid and trifluoroacetic acid and examples of suitable bases include guanidine, piperidine, morpholine, p-toluidine and 2-picoline, etc. Guanidine trichloroacetate as described in U.S. Pat. No. 3,220,846 is particularly preferred. Further, aldonic amides as described in Japanese Patent Application (OPI) No. 22625/75 are preferably used because they decompose at a high temperature to form bases.

It is advantageous to use a compound (development accelerator) represented by the general formula described below in the heat-developable color photographic material in order to accelerate development and accelerate release of a dye:

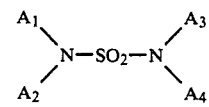

wherein $A_1$, $A_2$, $A_3$ and $A_4$, which may be the same or different, each represents a hydrogen atom or a substituent selected from the group consisting of an alkyl group, a substituted alkyl group, a cycloalkyl group, an aralkyl group, an aryl group, substituted aryl group and a heterocyclic group; and $A_1$ and $A_2$ or $A_3$ and $A_4$ may combine with each other to form a ring.

The development accelerator can be generally obtained by a reaction of a sulfamoyl chloride derivative described below with an amine as illustrated in the following scheme.

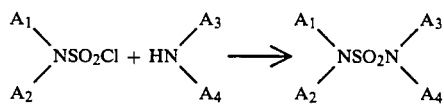

The sulfamoyl chloride derivative which is one of the raw materials can be easily obtained from the corresponding amine and sulfuryl chloride according to the method described in the literature, for example, *Ann. Chem.*, vol. 729, pages 40 to 51 (1969), etc. The condensation reaction of a sulfamoyl chloride derivative with an amine is usually carried out in an aprotic solvent such as acetonitrile, ether, tetrahydrofuran, etc., at a temperature of 20° C. to 50° C. using an excess amount of the amine whereby the desired compound can be obtained in a high yield. Synthesis example of the compound according to the present invention is specifically described below. Details of the development accelerator are set forth in U.S. Pat. No. 4,473,631, which disclosure is incorporated herein by reference.

The above-described development accelerator can be used in a broad range of amounts. A useful range is up to about 20% by weight based on the weight of a dry layer coated of the light-sensitive material. A range of 0.1% by weight to 15% by weight is more preferred.

It is advantageous to use a water releasing compound in the present invention in order to accelerate the dye releasing reaction.

The water releasing compound means a compound which releases water upon decomposition during heat development. These compounds are particularly known in the field of printing of fabrics, and NH$_4$Fe(SO$_4$)$_2$.12-

H₂O, etc., as described in Japanese Patent Application (OPI) NO. 88386/75 are useful.

Further, in the present invention, it is possible to use a compound which activates development simultaneously while stabilizing the image. Particularly, isothiuroniums including 2-hydroxyethylisothiuronium trichloroacetate as described in U.S. Pat. No. 3,301,678, bisisothiuroniums including 1,8-(3,6-dioxaoctane)-bis-(isothiuronium trifluoroacetate), etc., as described in U.S. Pat. No. 3,669,670, thiol compounds as described in German Patent Application (OLS) No. 2,162,714, thiazolium compounds such as 2-amino-2-thiazolium trichloroacetate, 2-amino-5-bromoethyl-2-thiazolium trichloroacetate, etc, as described in U.S. Pat. No. 4,012,260, compounds having α-sulfonylacetate as an acid moiety such as bis(2-amino-2-thiazolium)-methylenebis(sulfonylacetate), 2-amino-2-thiazolium phenylsulfonylacetate, etc., as described in U.S. Pat. No. 4,060,420, and compounds having 2-carboxycarboxamide as an acid part as described in U.S. Pat. No. 4,088,496 are preferred for use.

In the present invention, it is possible to use a thermal solvent. The term "thermal solvent" means a non-hydrolyzable organic material which is solid at ambient temperature but melts together with the other components at a temperature of the heat treatment or below. Preferred examples of thermal solvents include compounds acting as a solvent for the developing agent and compounds having a high dielectric constant which accelerate physical development of silver salts. Examples of preferred thermal solvents include those described in European Patent Application (OPI) No. 76,492.

In the present invention, though it is not very necessary to further incorporate substances or dyes for preventing irradiation or halation in the light-sensitive material, because the light-sensitive material is colored by the dye releasing redox compound, it is possible to use filter dyes or light absorbing materials, etc., as described in Japanese Patent Publication No. 3692/73 and U.S. Pat. Nos. 3,253,921, 2,527,583 and 2,956,879, etc., in order to further improve the sharpness. Preferably these dyes have a thermal bleaching property. For example, the dyes as described in U.S. Pat. Nos. 3,769,019, 3,745,009 and 3,615,432 are preferred.

Various means of exposure can be used in the present invention. Latent images are obtained by imagewise exposure to radiant light including visible rays. Generally, light sources used for conventional color prints can be used, examples of which include tungsten lamps, mercury lamps, halogen lamps such as iodine lamps, xenon lamps, laser light sources, CRT light sources, fluorescent tubes and light-emitting diodes, etc.

In the present invention, simultaneously with or after the heat-developable color photographic material is exposed to light, the resulting latent image can be developed by heating the entire material to a suitably elevated temperature, for example, about 80° C. to about 250° C. for about 0.5 second to about 300 seconds. A higher temperature or lower temperature can be utilized with heating time, if it is within the above-described temperature range, being prolonged or shortened. Particularly, a temperature range of about 110° C. to about 160° C. is useful.

A simple heat plate, iron, heat roller, heat generator utilizing carbon or titanium white, etc., or analogues thereof may be used as the heating means.

The present invention also provides a method for providing a color image which comprises imagewise exposing the heat developable color photographic material described above, i.e., comprising a support having thereon at least a photosensitive silver halide, a binder, a dye releasing material which is reductive to the photosensitive silver halide and releases a hydrophilic mobile dye upon reaction with the photosensitive silver halide by heating, and a base precursor represented by formula (I) or (II) described above, in a substantially water-free state; and subjecting the imagewise exposed photosensitive silver halide to heat development to release said hydrophilic mobile dye, whereby said hydrophilic mobile dye is viewed as a dye image separatedly from a silver image by an optical or physical means.

By providing the specific method for viewing the color image separatedly from the silver image, the system of the present invention is free from the prior art problems which might be caused by the co-present silver image or unexposed and undeveloped light-sensitive materials.

In the present invention, a specific means for forming a color image, which is to be viewed separatedly from a silver image, by heat development comprises providing a white background for viewing the color image and to mask the developed silver halide or transfer of the hydrophilic mobile-dye through a transparent support against the white background. The white background is typically provided by white pigments such as titanium dioxide, generally by forming a layer of titanium dioxide on a transparent support. For the latter purpose, the heat developable color photographic material of the present invention comprises a support having thereon a light-sensitive layer (I) containing at least a silver halide, a binder, a dye releasing material and a base precursor, and a dye fixing layer (II) capable of receiving the hydrophilic diffusible dye formed in the light-sensitive layer (I).

The above described light-sensitive layer (I) and the dye fixing layer (II) may be formed on the same support, or they may be formed on different supports, respectively. The dye fixing layer (II) can be stripped off the light-sensitive layer (I). For example, after the heat-developable color photographic material is exposed imagewise to light, it is developed by heating uniformly and thereafter the dye fixing layer (II) or the light-sensitive layer (I) is peeled apart. Also, when a light-sensitive material having the light-sensitive layer coated on a support and a fixing material having the dye fixing layer (II) coated on a support are separately formed, after the light-sensitive material is exposed imagewise to light and uniformly heated, the mobile dye can be transferred to the dye fixing layer (II) by superposing the fixing material on the light-sensitive material.

Further, a method wherein only the light-sensitive layer (I) is exposed imagewise to light and the heated uniformly by superposing the dye fixing layer (II) on the light-sensitive layer (I) can be used.

The dye fixing layer (II) can contain, for example, a dye mordant in order to fix the dye. In the present invention, various mordants can be used, and polymer mordants are particularly preferred. In addition to the mordants, the dye fixing layer may contain bases, base precursors and thermal solvents as previously discribed. In particular, incorporation of the bases or base precursors into the dye fixing layer (II) is particularly preferred where the light-sensitive layer (I) and the dye fixing layer (II) are formed on different supports.

Polymer mordants which can be used in the present invention are polymers containing secondary and tertiary amino groups, polymers containing nitrogen-containing heterocyclic moieties, polymers with quaternary cation groups thereof, having a molecular weight of from about 5,000 to 200,000, and particularly from 10,000 to 50,000.

For example, vinylpyridine polymers and vinylpyridinium cation polymers as disclosed in U.S. Pat. Nos. 2,548,564, 2,484,430, 3,148,061 and 3,756,814; etc., polymer mordants capable of cross-linking with gelatin as disclosed in U.S. Pat. Nos. 3,625,694, 3,859,096 and 4,128,538, British Pat. No. 1,277,453, etc., aqueous sol type mordants as disclosed in U.S. Pat. Nos. 3,958,995, 2,721,852 and 2,798,063, Japanese Patent Application (OPI) Nos. 115228/79, 145529/79 and 126027/79, etc., water-insoluble mordants as disclosed in U.S. Pat. No. 3,898,088, etc., reactive mordants capable of forming covalent bonds with dyes used as disclosed in U.S. Pat. No. 4,168,976 (Japanese Patent Application (OPI) No. 13733/79, etc., and mordants disclosed in U.S. Pat. Nos. 3,709,690, 3,788,855, 3,642,482, 3,488,706, 3,557,066, 3,271,147 and 3,271,148, Japanese Patent Application (OPI) Nos. 71332/75, 30328/78, 155528/77, 125/78 and 1024/78, etc., are illustrative.

In addition, the mordants disclosed in U.S. Pat. Nos. 2,675,316 and 2,882,156 can be used.

The dye fixing layer (II) can have a white reflective layer. For example, a layer of titanium dioxide dispersed in gelatin can be provided on the mordant layer on a transparent support. The layer of titanium dioxide forms a white opaque layer, by which reflection color images of the transferred color images which is observed through the transparent support are obtained.

A typical dye fixing material used in the present invention is obtained by mixing a polymer containing ammonium salt groups with gelatin and applying the mixture to a transparent support.

The transfer of dye from the light-sensitive layer to the dye fixing layer can be carried out using a dye transfer assistant. Examples of useful dye transfer assistants include water and an alkaline aqueous solution containing sodium hydroxide, potassium hydroxide and an inorganic alkali metal salt. Further, a solvent having a low boiling point such as methanol, N,N-dimethylformamide, acetone, diisobutyl ketone, etc., and a mixture of such a solvent having a low boiling point with water or an alkaline aqueous solution can be used. The dye transfer assistant can be employed by wetting the image receiving layer with the transfer assistant or by incorporating it in the form of water of crystallization or microcapsules into the material.

Unless otherwise indicated all parts, ratios and percentages are by weight.

EXAMPLE 1

In 3,000 ml of water were dissolved 40 g of gelatin and 26 g of potassium bromide and the solution was stirred at 50° C. Then, a solution of 34 g of silver nitrate in 200 ml of water was added to the foregoing solution over a period of 10 minutes and thereafter a solution of 3.3 g of potassium iodide in 100 ml of water was added thereto over a period of 2 minutes.

The pH of the silver iodobromide emulsion was controlled to precipitate excessive salts, which were removed. Thereafter, the pH of the emulsion was adjusted to 6.0 to provide 400 g of a silver iodobromide emulsion.

Then, a selating dispersion of a dye-releasing material was prepared as follows.

To 30 ml of ethyl acetate were added 5 g of Dye-Releasing Material (2) shown below, 0.5 g of a surface active agent, succinic acid-2-ethyl-hexyl ester sodium sulfonate, and 5 g of tricresyl phosphate and the mixture was heated to about 60° C. to form a solution. The solution was mixed with 100 g of a 10% gelatin aqueous solution with stirring and the resultant mixture was treated in a homogenizer at 10,000 r.p.m. for 10 minutes to form a dispersion. The dispersion was a dispersion of dye-releasing material.

Dye Releasing Material (2)

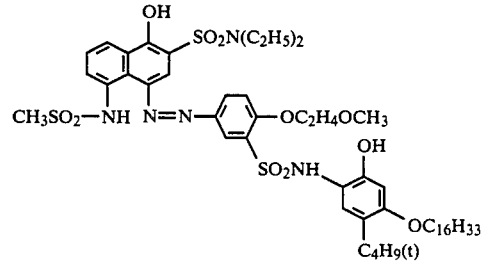

Then, a light-sensitive material was prepared as follows.

| | |
|---|---|
| (a) Photosensitive Silver Iodobromide Emulsion (as described above) | 25 g |
| (b) Dispersion of Dye-Releasing Material (as described above) | 33 g |
| (c) 5% Aqueous Solution of the Following Compound | 10 ml |
| 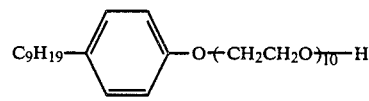 | |
| (d) 10% Aqueous Solution of the Following Compound H$_2$NSO$_2$N(CH$_3$)$_2$ | 4 ml |
| (e) Solution of 3 g of Base Precursor (1) of this invention in 30 ml of 50:50 vol % water-methanol mixture | |

A mixture of the foregoing components (a) to (e) was heated to form a solution and the solution was coated on a polyethylene terephthalate film of a thickness of 180 μm at a wet thickness of 30 μm to provide a light-sensitive coated material.

After drying, the coated sample was imagewise exposed to light from tungsten lamp at 2,000 lux for 10 seconds and thereafter, the sample was uniformly heated on a heat block heated to 150° C. for 30 seconds to provide Sample A.

Then, by following the same procedure as used in producing Sample A except that 30 ml of 50:50 vol% water-methanol was used in place of component (e) above containing Base Precursor (1) of this invention, Sample B was prepared.

Further, Sample X was prepared by following the same procedures as used in producing Sample A except that 3.6 g (equimolar amount) of 2-amino-2-thiazolium phenylsulfonylacetate (Compound 1 of U.S. Pat. No. 4,060,420 at column 6) was used in place of Base Precursor (1) of this invention in component (e).

An image-receiving material having an image-receiving layer was prepared as follows.

In 200 ml of water was dissolved 10 g of polymethyl acrylate-co-N,N,N,-trimethyl-N-vinylbenzylammonium chloride (the weight ratio of methyl acrylate and vinylbenzylammonium chloride was 1:1) and the solution was uniformly mixed with 100 g of a 10% aqueous solution of lime-treated gelatin. The mixture was uniformly coated on a paper support having laminated thereon a layer of polyethylene with titanium dioxide dispersed therein ain a wet thickness of 90 μm and dried to provide an image-receiving material.

After wetting the image-receiving material with water, each of the foregoing heated light-sensitive materials, Samples A, B and X, was superposed on the image-receiving material so that the coated layers were in a face-to-face relationship.

After heating the assembly on a heat block heated to 80° C. for 6 seconds, the image-receiving material was separated from the light-sensitive material, a negative magenta dye image was obtained on the image-receiving material. When the density of the negative image was measured using a Macbeth reflection densitometer (RD-519), the following results were obtained.

| Sample No. | Base Precursor | Maximum Density | Minimum Density |
| --- | --- | --- | --- |
| A (This Invention) | Base Precursor (1) | 1.95 | 0.20 |
| B (Comparison) | — | 0.03 | 0.03 |
| X (Comparison) | Compound 1 of U.S.P. 4,060,420 | 0.20 | 0.03 |

From the above results, it can be seen that Sample A using the base precursor of this invention characterized by containing heterocyclic N but containing no heterocyclic S in the molecule results in high density. On the other hand, Sample B containing no base precursor provides the same density in the both maximum and minimum densities. This means that no images are formed. Further Sample X provides only vague images which are hardly discernible with the eye since Compound 1 contained heterocyclic S in the molecule, even though compound 1 used in Sample X could release a base.

Furthermore, when Sample A was stored for 2 days at 60° C. and then precessed in the same manner as described above, the minimum density and the maximun density were 0.28 and 1.99, respectively, which indicates that the sample of this invention also has excellent shelf life.

EXAMPLE 2

By following the same procedure as described in Example 1 except that the base precursors shown in the table below were used in the amounts shown in the same table, the following results were obtained.

| Sample No. | Base Precursor | Maximum Density |
| --- | --- | --- |
| C | Compound (2) 3.0 g | 1.72 |
| D | Compound (3) 3.0 g | 1.80 |
| E | Compound (4) 3.0 g | 1.92 |
| F | Compound (5) 3.0 g | 1.89. |
| G | Compound (6) 3.0 g | 1.70 |
| H | Compound (7) 3.0 g | 1.77 |
| I | Compound (24) 3.0 g | 1.93 |

From the above results, it can be seen that the base precursors of this invention have excellent effects.

EXAMPLE 3

By following the same procedure as described in Example 1 except that each of the following dye-releasing materials was used in place of the Dye-Releasing Material (2) in Example 1, the following dispersions of dye-releasing materials were prepared.

| Dye-Releasing Material (8) | 5 g | Dispersion (I) |
| --- | --- | --- |
| Dye-Releasing Material (4) | 7.5 g | Dispersion (II) |
| Dye Releasing Material (12) | 5 g | Dispersion (III) |

Dye-Releasing Material (8)

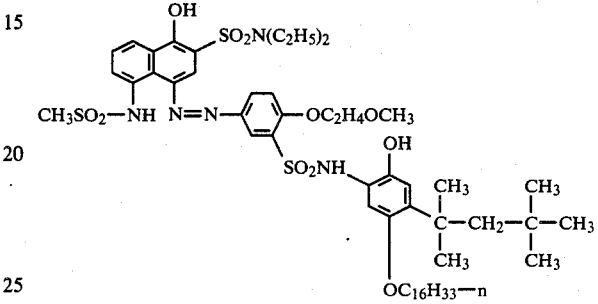

Dye-Releasing Material (4)

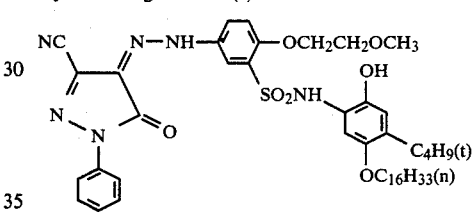

Dye-Releasing Material (12)

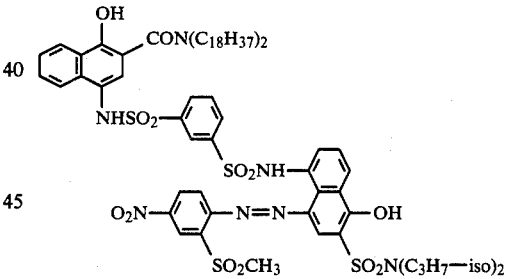

Also, by following the same procedure as described in Example 1, light-sensitive samples were prepared and they were processed as described in Example 1. The results obtained are shown in the following table.

| Dispersion of Dye-Releasing Material | Compound (1) of this Invention | Maximum Density | Minimum Density |
| --- | --- | --- | --- |
| Dispersion (I) | Used | 1.90 | 0.18 |
| (Magenta) | None | 0.03 | 0.03 |
| Dispersion (II) | Used | 1.67 | 0.22 |
| (Yellow) | None | 0.03 | 0.03 |
| Dispersion (III) | Used | 2.03 | 0.37 |
| (Cyan) | None | 0.20 | 0.05 |

From the above results, it can be seen that the base precursors of this invention provide image with high maximum density.

EXAMPLE 4

The following example illustrates the use of an organic silver salt oxidizing agent.

Preparation of benzotriazole silver salt emulsion:

In 3,000 ml of water were dissolved 28 g of gelatin and 13.2 g of benzotriazole and the solution was stirred at 40° C. To the solution was added a solution of 17 g of silver nitrate in 100 ml of water over a period of two minutes.

The pH of the benzotriazole silver salt emulsion was controlled to precipitate excessive salts, which were then removed. Thereafter, the pH of the emulsion was adjusted to 6.0 to provide 400 g of a benzotriazole silver salt emulsion.

A light-sensitive material was prepared as follows using the benzotriazole silver salt emulsion.

| | |
|---|---|
| (a) Silver Iodobrimide Emulsion (as described in Example 1) | 20 g |
| (b) Benzotriazole Silver Salt Emulsion | 10 g |
| (c) Dispersion of Dye-Releasing Material (2) (as described in Example 1) | 33 g |
| (d) 5% Aqueous Solution of the Following Compound | 10 ml |

$C_9H_{19}$—⟨benzene⟩—$O$—$(CH_2CH_2O)_{\overline{10}}$—$H$

| | |
|---|---|
| (e) 10% Aqueous Solution of the Following Compound $H_2NSO_2N(CH_3)_2$ | 4 ml |
| (f) Solution of 3 g of Base Precursor (1) of this invention in 30 ml of 50:50 vol % Water-Methanol Mixture | |

The foregoing components (a) to (f) were mixed and by following the same procedure as described in Example 1 using the mixture, a light-sensitive sample was prepared. The sample was processed as described in Example 1. The results obtained are shown below together with results of a comparison sample prepared using the same method as above but without using the base precursor.

| Sample | Maximum Density | Minimum Density |
|---|---|---|
| Sample of This Invention (containing Base Precursor (1) of this invention) | 2.11 | 0.20 |
| Comparison Sample (without any base precursor) | 0.03 | 0.03 |

From the above results, it can be seen that the base precursor of this invention provides images with high density.

EXAMPLE 5

Preparation of Silver Iodobromide Emulsion

Gelatin (40 g) and KBr (26 g) were dissolved in water (3,000 ml). The solution was agitated at 50° C. A solution obtained by dissolving silver nitrate (34 g) in water (200 ml), and a solution (200 ml) obtained by dissolving dye I (0.02 g) shown hereinafter to 300 ml mathanol were added to the KBr solution over a period of 10 minutes. To this solution, a solution of KI (3.3 g) in water (100 ml) was added over a period of 2 minutes. The pH of the thus prepared silver idobromide emulsion was adjusted to precipitate the emulsion and the excess salt was then filtered out. The pH of the emulsion was adjusted to 6.0 to obtain a silver iodrobomide emulsion (yield: 400 g).

Preparation of Coupler Dispersion in Gelatin 2-dodecylcarbamoyl-1-naphthol (dye providing material (17) 5 g), succinic acid-2-ethylhexyl ester sodium sulfonate (0.5 g) and tricresyl phosphate (TCP) (2.5 g) were dissolved in ethyl acetate (30 ml). The resulting solution was mixed with a 10 wt% gelatin solution (100 g) under agitation, and, the mixture was dispersed using a homogenizer for 10 minutes at 10,000 rpm.

A coating liquid having the composition indicated below was applied to a polyethylene terephthalate film base to give a wet thickness of 60 μm and then dried to prepare a light-sensitive material.

| | |
|---|---|
| (a) Silver iodobromide emulsion | 10 g |
| (b) Coupler dispersion in gelatin | 3.5 g |
| (c) Solution of base precursor (101) of the present invention | 0.28 g |
| (d) Gelatin (10 wt % aq. sol.) | 5 g |
| (e) Solution of 0.2 g of 2,6-dichloro-p-aminophenol dissolved in 17 ml of water | |

The light-sensitive material thus prepared was imagewise exposed using a tungsten lamp (2,000 lux) for 5 seconds. Then, the exposed material was heated uniformly on a heat block (150° C., 20 sec) to provide a negative cyan dye image. The image density was measured with a Macbeth transmission densitometer (Model TD-504): Dmin was 0.26 and Dmax was 2.13.

The above result indicates that the base precursor according to the present invention provides a high density.

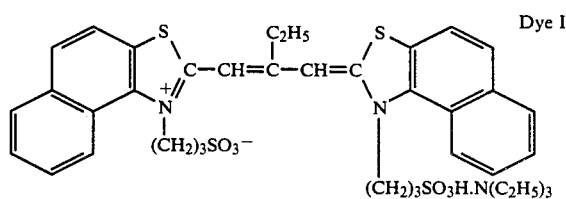

Dye I

EXAMPLE 6

In this example, a silver iodobromide emulsion of the same type as used in Example 5, and a dispersion of dye releasing material prepared as follows were used.

Preparation of Dispersion of Dye Releasing Material

Five grams of a dye releasing material (2) and 0.5 g of surfactant i.e. succinic acid-2-ethylhexyl ester sodium sulfonate and 5 g of tricresyl phosphate (TCP) were dissolved in 30 ml of ethyl acetate under heating at about 60° C. The resulting solution was mixed with a 10 wt% gelatin solution (100 g) under agitation, and the resulting mixture was dispersed using a homogenizer for 10 minutes at 10,000 rpm.

A light-sensitive composition was prepared from the following formulation.

| | | |
|---|---|---|
| (a) | Light-sensitive silver iodobromide emulsion (as shown in Example 1) | 25 g |
| (b) | Dispersion of dye releasing material (2) | 33 g |
| (c) | 5 wt % Aqueous solution of the following compound: | 10 ml |

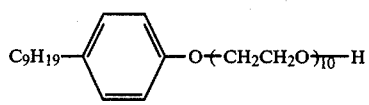

| | | |
|---|---|---|
| (d) | 10 wt % Aqueous solution of the following compound: H₂NSO₂N(CH₃)₂ | 4 ml |
| (e) | Base precursor (101) of the present invention | 2.7 g |
| (f) | Water | 20 ml |

The above components of (a)~(f) were mixed and dissolved under heating. The resulting solution was applied onto a polyethylene terephthalate film base to give a wet thickness of 30 μm and then dried to provide a light-sensitive material. This material was imagewise exposed using a tungsten lamp (2,000 lux) for 10 seconds and heated uniformly on a heat block (150° C.) for 20 seconds to provide sample AA.

Sample BB was prepared by following the same procedure as above except that 1.8 g of guanidinetrichloroacetic acid was used in place of the compound of this invention of (e) in Sample AA, Sample CC was prepared using 2.1 g of guanidine phenulsulfonylacetate in place of the aforesaid compound of this invention, and Sample DD was prepared using 2.2 g of guanidine 3-sulfamoylphenylsulfonylacetate in place of the aforesaid compound of this invention and these samples were processed by the same manner as above.

Preparation of Image-receiving Material

Ten grams of methyl acrylate-N,N,N-trimethyl-N-vinyl-benzylammonium chloride copolymer (molar ratio of methyl acrylate to vinyl benzyl ammonium chloride is 1:1) was dissolved in water (200 ml), and the solution was mixed uniformly with 10 wt% lime-treated gelatin (100 g). The resulting mixture was uniformly spread onto a paper base laminated with TiO₂ dispersed polyethylene, thereby forming an image-receiving layer of a uniform wet thickness of 90 μm. The layer was dried to provide an image-receiving material.

The image receiving material was dipped in water and recovered therefrom. Samples AA, BB, CC and DD of the light-sensitive material heated were superimposed on each sample of image-receiving material in such a manner that each of the light-sensitive layers was in contact with the image-receiving layer, respectively.

After heating on a heat block (80° C.) for 6 seconds, each image-receiving material was peeled from each light-sensitive material. A negative magenta image was formed on each image-receiving material. The density of each negative image was measured with a Macbeth (RD-519) reflection densitometer. The results were as follows.

| Sample No. | Dmax | Dmin |
|---|---|---|
| AA (Present Invention) | 1.95 | 0.15 |
| BB (Control) | 2.14 | 0.58 |
| CC (Control) | 1.28 | 0.16 |
| DD (Control) | 1.45 | 0.15 |

The above results show that the base precursor according to the present invention gives high maximum and low minimum densities.

Samples AA, BB, CC and DD were left to stand at 60° C. for 2 days, and treated as above. The Dmin and Dmax of the image of Sample AA were 0.23 and 2.01, Sample CC were 0.20 and 1.33 and Sample DD were 0.27 and 1.49 respectively, but fog occurred throughout the surface of Sample BB. Thus, the Sample of the present invention has an improved storage stability.

EXAMPLE 7

The procedure of Example 6 was repeated except that the base precursors shown in the following table were used. The results are also shown in the same table.

| Sample No. | Base Precursor (g) | Dmax |
|---|---|---|
| DD | Compound (102) 2.8 | 2.03 |
| EE | Compound (106) 2.5 | 1.79 |
| FF | Compound (109) 3.0 | 1.92 |
| GG | Compound (115) 3.2 | 2.00 |
| HH | Compound (116) 3.3 | 2.12 |
| II | Compound (121) 2.3 | 1.83 |
| JJ | Compound (123) 3.8 | 1.82 |
| KK | Compound (125) 3.5 | 1.99 |

The above results show that base precursors according to the present invention give high maximum densities.

EXAMPLE 8

In this example, an organic silver salt oxidizing agent was used.

Preparation of Silver Benzotriazole Emulsion

Gelatin (28 g) and benzotriazole (13.2 g) were dissolved in water (3,000 ml). The resulting solution was agitated at 40° C. To this solution, a solution having silver nitrate (17 g) dissolved in water (100 ml) was added over a period of 2 minutes.

The resulting benzotriazole silver emulsion was pH-adjusted to precipitate, and the excess salt was filtered out. The emulsion was adjusted to a pH of 6.0, thereby providing a silver benzotriazole emulsion (yield: 400 g).

Using this silver benzotriazole emulsion, a light-sensitive coating composition was prepared from the following formulation.

| | | |
|---|---|---|
| (a) | Silver iodobromide emulsion (as prepared in Example 5) | 20 g |
| (b) | Silver benzotriazole emulsion | 10 g |
| (c) | Dispersion of dye releasing material (as prepared in Example 6) | 33 g |
| (d) | 5% Aqueous solution of the following compound: | 10 ml |

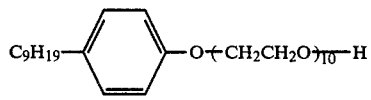

| | | |
|---|---|---|
| (e) | 10% Aqueous solution of the following compound: H₂NSO₂N(CH₃)₂ | 4 ml |
| (f) | Base precursor (101) of the present invention | 3 g |
| (g) | Gelatin dispersion of the acid precursor shown below | 8 ml |
| (h) | Water | 12 ml |

The gelatin dispersion of the acid precursor of the aforesaid component (g) was prepared as follows.

To 100 g of 1% aqueous solution of gelatin was added 10 g of the compound shown below and the compound was pulverized for 10 minutes in a mill using 100 g of glass beads having a mean particle size of about 0.6 mm. By separating the glass beads by filtration, a gelatin dispersion of the acid precursor was obtained.

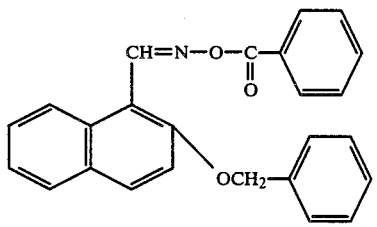

Above components (a) to (g) were mixed and by following the same procedure as in Example 6 using the mixture, Samples AA', BB' and CC' were prepared. The samples were also processed as in Example 6 and the results thus obtained are shown below.

| Sample | Dmax | Dmin |
|---|---|---|
| A Containing Base Precursor (101) (This invention) | 2.19 | 0.16 |
| B Containing Guanidine-trichloroacetic Acid (Comparison) | 2.33 | 0.61 |
| C Containing Guanidine Phenylsulfonylacetate (Comparison) | 1.47 | 0.19 |

From the results, it can be seen that the sample of this invention containing the base precursor in this invention give both the high maximum density and the low minimum density.

Furthermore, after storing Samples AA', BB' and CC' for 2 days at 60° C., and then processing in the same manner as above and the results showed that the minimum density and the maximum density were 0.23 and 2.21, respectively for Sample AA' and 0.20 and 1.52, respectively for Sample CC', while Sample BB' was overall fogged. Thus, it can be seen that the sample of this invention show a good storage stability.

EXAMPLE 9

Preparation of Silver Benzotriazole Emulsion Containing Light-sensitive Silver Bromide Benzotriazole (6.5 g) and gelatin (10 g) were dissolved in water (1,000 ml). The resulting solution was agitated at 50° C. To this solution, a solution of silver nitrate (8.5 g) dissolved in water (100 ml) was added over a period of 2 minutes.

Then, a solution of potassium bromide (1.2 g) dissolved in water (50 ml) was added to the above-obtained solution over a period of 2 minutes. The thus prepared emulsion was pH-adjusted to precipitate, and the excess salt was filtered out. The emulsion was adjusted to a pH of 6.0, thereby providing a silver benzotriazole emulsion (yield: 200 g).

Preparation of Gelatin Dispersion of Dye Releasing Material (16)

Ten grams of a dye releasing material (16) of the following formula:

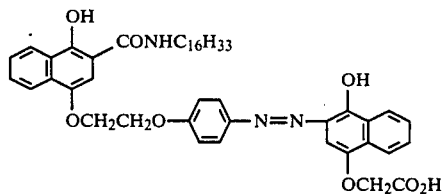

and 0.5 g of a surfactant i.e., succinic acid-2-ethylhexyl ester sodium sulfate, and 4 g of tricresyl phosphate (TCP) were dissolved in 20 ml of cyclohexanone under heating at about 60° C., thereby producing a uniform solution. This solution was mixed with a 10 wt% solution of lime-treated gelatin (100 g) under agitation, and the mixture was dispersed with homogenizer for 10 minutes at 10,000 rpm.

A coating composition for light-sensitive material was prepared from the following formulation.

| (a) Silver benzotriazole emulsion containing light-sensitive silver bromide | 10 g |
|---|---|
| (b) Dispersion of dye releasing material | 3.5 g |
| (c) Base precursor (101) of the present invention | 0.28 g |
| (d) Gelatin (10 wt % aq. sol.) | 5 g |
| (e) Solution having 2,6-dichloro-4-aminophenol (200 ml) dissolved in methanol (4 ml) | |

The above components of (a)–(e) were mixed and dissolved under heating. The resulting solution was applied to a polyethylene terephthalate film base (180 μm thick) to form a light-sensitive layer having a wet thickness of 30 μm. The resulting web was dried and imagewise exposed using a tungsten lamp (200 lux) for 10 seconds and subsequently heated uniformly on a heat block (150° C.) for 20 seconds.

The heated sample of light-sensitive material was superimposed on an image-receiving material prepared in Example 6, and subsequently processed as in Example 6 to provide a negative magenta image on the image-receiving material. Measurement with a reflection densitometer showed that the negative image had Dmax 2.06 and Dmin 0.20.

Thus it was found that the compound of the present invention provides excellent effects.

EXAMPLE 10

Preparation of Gelatin Dispersion of Dye Releasing Material

Five grams of each of reducible dye releasing materials of

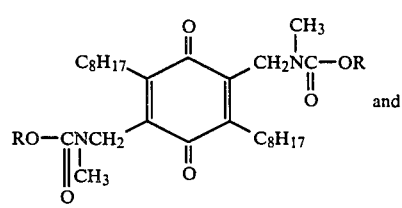

-continued

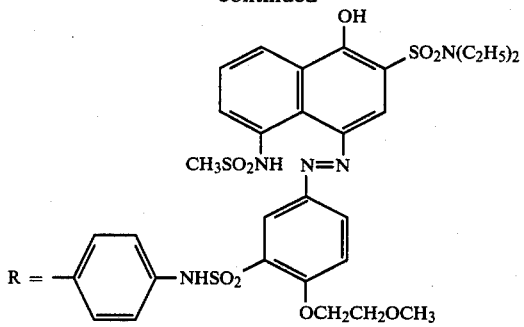

four grams of the electron donor having the following formula:

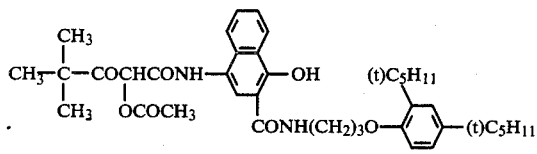

and 0.5 g of succinic acid-2-ethylhexyl ester sodium sulfate, and 10 g of tricresyl phosphate (TCP) were dissolved in 20 ml of cyclohexanone under heating at about 60° C. This solution was mixed with a 10 wt% solution of gelatin (100 g) under agitation, and the mixture was dispersed with homogenizer for 10 minutes at 10,000 rpm.

A coating composition for light-sensitive material was prepared from the following formulation.

| | | |
|---|---|---|
| (a) | Silver benzotriazole emulsion containing light-sensitive silver bromide (obtained in Example 9) | 10 g |
| (b) | Dispersion of dye releasing material (obtained in this Example) | 3.5 g |
| (c) | Base precursor (101) of the present invention | 0.4 g |
| (d) | 5% Aqueous solution of the following compound: | 1.5 ml |

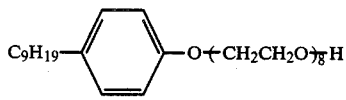

To the above components of (a)–(d) were added 4 ml of water, mixed and dissolved under heating. The resulting solution was applied to a polyethylene terephthalate film base to form a light-sensitive layer having a wet thickness of 30 μm. The resulting web was dried and imagewise exposed using a tungsten lamp (2000 lux) for 10 seconds and subsequently heated uniformly on a heat block (140° C.) for 40 seconds.

The heated sample of light-sensitive material was superimposed on an image-receiving material prepared in Example 6 previously impregnated with water, and subsequently processed as in Example 6 to provide a positive magenta image on the image-receiving material. Measurement with a reflection densitometer using green light showed that the image had Dmax 1.92 and Dmin 0.26.

Thus it was found that the base precursor of the present invention provides excellent effects.

While the invention has been described in detail and with reference to specific embodiments thereof, it will be apparent to one skilled in the art that various changes and modifications can be made therein without departing from the spirit and scope thereof.

What is claimed is:

1. A heat developable photographic material comprising a support having thereon at least a photo sensitive silver halide, a binder, a dye-providing material which releases or produces a hydrophilic mobile dye corresponding to or reversely corresponding to a reduction reaction of the photosensitive silver halide by heating, and at least one base precursor selected from the group consisting of compounds represented by following formula (I):

$$[R + SO_2CH_2COOH)_x]_z \cdot By \qquad (I)$$

wherein R represents a substituted or unsubstituted alkyl group, a substituted or unsubstituted alkylene group, a substituted or unsubstituted aryl group, a substituted or unsubstituted arylene group, a substituted or unsubstituted monovalent or divalent heterocyclic group; B represents a mono- or di-acidic nitrogen-containing, sulfur-free base having a pKa of not lower than 7 and containing 12 carbon atoms or less; x is an integer of 1 when R represents a monovalent group or an integer of 2 when R represents a divalent group, y is the same as x when B represents the mono-acidic base or an integer of 1 when B represents the di-acidic base; and z is an integer of 2 when R represents a monovalent group and B represents the di-acidic base or otherwise an integer of 1; whereby stability with the passage of time prior to heat development is improved.

2. The photographic material of claim 1, wherein R is an aryl group, an arylene group, a heterocyclic group or substituted groups of these groups with one or more substituents.

3. The photographis material of claim 1, wherein R is an aryl group, a heterocyclic group, or substituted groups of these groups with an electron attracting group having a Hammet sigma value of above 0.

4. The photographic material of claim 3, wherein said electron attracting group is a halogen atom, a cyano group, a nitro group, a carbamoyl group, a substituted carbamoyl group, a sulfamoyl group, a substituted sulfamoyl group, sulfonyl group, or an alkoxycarbonyl group.

5. The photographic material of claim 1, wherein said base represented by B is a base having a pKa value of not lower than 7 with a boiling point of not lower than about 150° C.

6. The photographic material of claim 1, wherein said B is a dialkylamine, a cyclic amine, a guanidine, a cyclic quanidine, an amidine, a cyclic amidine or a tetraalkyl ammonium hydroxide.

7. The photographic material of claim 1, wherein said B is selected from the group consisting of dimethylamine, diethylamine, piperidine, piperazine, ethylenediamine, N,N'-dimethylethylenediamine, acetoamidine, diazabicyclononene, diazabicycloundecene, tetramethylammonium hydroxide, tetraethylammonium hydroxide,

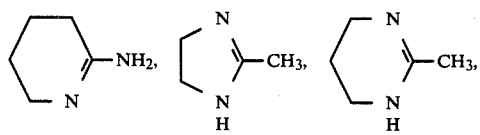

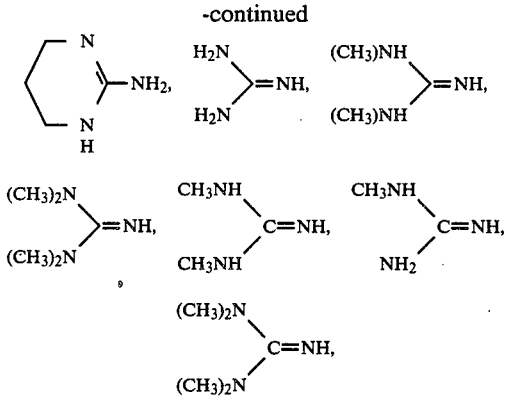

N,N,N',N'-tetramethylenediamine, and N,N,N',N'-tetramethyltetramethylenediamine.

8. The photographic material of claim 1, wherein said base precursor is represented by following formula (I'):

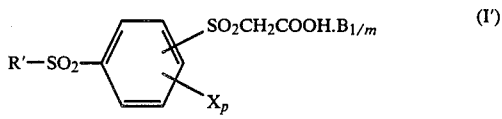

wherein R' represents a substituted or unsubstituted alkyl group, a substituted or unsubstituted cycloalkyl group, a substituted or unsubstituted alkenyl group, a substituted alkynyl group, a substituted or unsubstituted aralkyl group, a substituted or unsubstituted aryl group or a substituted or unsubstituted heterocyclic group; X represents a substituent, p represents an integer of 0 to 4 and B is as defined in claim 1 and m represents 1 when B represents the mono-acidic base and represents 2 when B represents the di-acidic base.

9. The photographic material of claim 8, wherein the substituent of said substituted group represented by R' is selected from the group consisting of an alkyl group, an alkyl- or arylsulfonyl group, a sulfamoyl group, an N-alkyl- or N-arylsulfamoyl group, a carbamoyl group, an N-alkyl- or N-arylcarbamoyl group, an alkyl or arylsulfonamido group, an alkyl- or arylcarbonyl amido group, a halogen atom, $—OM_{1/m'}$, $—COOM_{1/m'}$, and $—OH·B_{1/m}$ (wherein —OH is phenolic), $—COOH·B_{1/m}$, wherein M, B, m and m' have same definitions as defined in claim 8.

10. The photographic material of claim 9, wherein M represents an atom selected from the group consisting of Na, K, Cs and Ba.

11. The color photographic material of claim 8, wherein X represents a group or atom selected from the group consisting of a hydrogen atom, a halogen atom, an alkyl group, a cycloalkyl group, an aralkyl group, an alkoxy group, an aryloxy group, an aryl group, an alkyl or aryl carbonylamino group, an alkyl or aryl carbonyl group, a cyano group, an alkylsulfonylamino group, a nitro group, an arylsulfonylamino group, an alkylsulfonyl group, an arylsulfonyl group, a sulfamoyl group, a substituted sulfamoyl group, a carbamoyl group, a substituted carbamoyl group, an alkylthio group, an arylthio group, an alkoxycarbonyl group, an aryloxycarbonyl group, an alkyl- or arylcarbonyloxy group, and substituted groups thereof at the alkyl or aryl moiety thereof, $—OM_{1/m'}$, $—COOM_{1/m'}$, $—OH·B_{1/m}$, $—COOH·B_{1/m}$, wherein M, B, m and m' have same deinitions as defined in claim 8.

12. The photographic material of claim 1, wherein said base precursor is incorporated in an amount of from 0.001 to 50% by wegiht based on the total weight of the dry coated layer of the light-sensitive material.

13. The photographic material of claim 1, wherein said silver halide emulsion containing a sensitizing dye.

14. The photographic material of claim 13, wherein the amount of the sensitizing dye is from 0.001 to 20 g per 100 g of silver of the silver halide emulsion.

15. The photographic material of claim 1, wherein said dye-providing material is selected from the group consisting of a coupler, a dye which is able to form positive color images by photographic silver dye bleaching process, a dye having introduced therein a nitrogen-containing heterocyclic ring group, a dye-providing material which releases a mobile dye by a coupling reaction with a reducing agent which is oxidized by an oxidation reduction reaction with a silver halide or an organic silver salt upon heat development, a non-diffusible image-forming compound which causes self ring closure to the presence of a base to release a diffusible dye, but does not release the dye when the compound reacts with the oxidation product of a developing agent, a non-diffusible image-forming compound which does not release a dye by itself but releases a dye when the compound reacts with a reducing agent, and a linked donor acceptor compound which is a nondiffusible image-forming compound and causes a donor-acceptor reaction in the presence of a base to release a diffusible dye, but does not substantially release the dye when the compound reacts with the oxidation product of a developing agent.

16. The photographic material of claim 1, wherein said base precursor is incorporated in the silver halide emulsion layer.

17. The photographic material of claim 1, wherein the photographic material further comprises an image fixing layer provided on a support other than that for the light-sensitive layer, and said base precursor is incorporated in the image fixing layer.

18. A method for producing a color image optically or physically separated from a silver image, which comprises exposing and heat developing a heat developable color photographic material comprising a support having provided thereon at least a photosensitive silver halide, a binder, a dye providing material which releases or produces a hydrophilic mobile dye corresponding to or reversely corresponding to a reduction reaction of the photosensitive silver halide by heating, and at least one base precursor selected from the group consisting of compounds represented by following formula (I):

wherein R represents a substituted or unsubstituted alkyl group, a substituted or unsubstituted alkylene group, a substituted or unsubstituted aryl group, a substituted or unsubstituted arylene group, a substituted or unsubstituted monovalent or divalent heterocyclic group; B represents a mono- or di-acidic, nitrogen-containing, sulfur-free base having a pKa of not lower than 7 and containing 12 carbon atoms or less; x is an integer of 1 when R represents a monovalent group or an integer of 2 when R represents a divalent group, y is the same as x when B represents the mono-acidic base or an integer of 1 when B represents the di-acidic base; and z is an integer of 2 when R represents a monovalent group and B represents the di-acidic base or otherwise an integer of 1.

19. A method for producing an image of claim 18, wherein said base precursor is represented by following formula (I'):

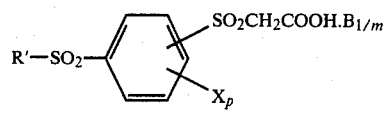

wherein R' represents a substituted or unsubstituted alkyl group, a substituted or unsubstituted cycloalkyl group, a substituted or unsubstituted alkenyl group, alkynyl group, a substituted or unsubstituted aralkyl group, a substituted or unsubstituted aryl group or a substituted or unsubstituted heterocyclic group; X represents a substituent, p represents an integer of 0 to 4 and B is as defined in claim 18, m represents 1 when B represents the mono-acidic base and represents 2 when B represents the di-acidic base.

20. A method for producing an image of claim 18, which comprises transferring the color image obtained by heat developing to an image fixing layer.

* * * * *